United States Patent
Fukudome et al.

(10) Patent No.: US 10,828,240 B2
(45) Date of Patent: Nov. 10, 2020

(54) LIGHT CURABLE COMPOSITION

(71) Applicant: TOKUYAMA DENTAL CORPORATION, Tokyo (JP)

(72) Inventors: Keishi Fukudome, Tokyo (JP); Hironobu Akizumi, Tokyo (JP)

(73) Assignee: TOKUYAMA DENTAL CORPORATION, Tokyo (JP)

( * ) Notice: Subject to any disclaimer, the term of this patent is extended or adjusted under 35 U.S.C. 154(b) by 0 days.

(21) Appl. No.: 16/328,984

(22) PCT Filed: Aug. 30, 2017

(86) PCT No.: PCT/JP2017/031244
§ 371 (c)(1),
(2) Date: Feb. 27, 2019

(87) PCT Pub. No.: WO2018/043595
PCT Pub. Date: Mar. 8, 2018

(65) Prior Publication Data
US 2019/0192386 A1    Jun. 27, 2019

(30) Foreign Application Priority Data

Aug. 31, 2016 (JP) ................................. 2016-169468

(51) Int. Cl.
C08F 2/46        (2006.01)
C08F 2/50        (2006.01)
C08G 61/04       (2006.01)
A61K 6/887       (2020.01)
A61K 6/71        (2020.01)
A61K 6/76        (2020.01)

(52) U.S. Cl.
CPC ................ A61K 6/887 (2020.01); A61K 6/71 (2020.01); A61K 6/76 (2020.01)

(58) Field of Classification Search
CPC ........ A61K 6/083; A61K 6/088; A61K 6/073; A61K 6/887; A61K 6/76; A61K 6/71; A61K 6/17; A61K 6/16; C08L 33/10
USPC ................. 522/47, 6, 71, 189, 184, 1; 520/1
See application file for complete search history.

(56) References Cited

U.S. PATENT DOCUMENTS

| 7,235,602 B2 | 6/2007 | Klettke et al. |
| 8,461,227 B2 | 6/2013 | Jin et al. |
| 9,320,684 B2 | 4/2016 | Isizaka et al. |
| 9,993,394 B2 | 6/2018 | Kita et al. |
| 2004/0186202 A1 | 9/2004 | Klettke et al. |
| 2006/0063854 A1 | 3/2006 | Jin et al. |
| 2013/0096226 A1 | 4/2013 | Toriyabe et al. |
| 2014/0206792 A1* | 7/2014 | Ishizaka .................. A61K 6/17 523/115 |
| 2015/0272833 A1 | 10/2015 | Toriyabe et al. |

FOREIGN PATENT DOCUMENTS

| JP | 62-86003 A | 4/1987 |
| JP | 2004-149587 A | 5/2004 |
| JP | 2004-527602 A | 9/2004 |
| JP | 2008-502697 A | 1/2008 |
| JP | 2009-540107 A | 11/2009 |
| JP | 2012-153640 A | 8/2012 |
| WO | 02/066535 A1 | 8/2002 |
| WO | 2006/002086 A1 | 1/2006 |
| WO | 2008/005173 A1 | 1/2008 |
| WO | 2012/176877 A1 | 12/2012 |
| WO | 2014/050634 A1 | 4/2014 |
| WO | 2015/125470 A1 | 8/2015 |

OTHER PUBLICATIONS

International Search Report dated Oct. 5, 2017, dated Oct. 17, 2017.
English translation of International Search Report dated Oct. 5, 2017, dated Oct. 17, 2017.

\* cited by examiner

Primary Examiner — Jessica Whiteley
(74) Attorney, Agent, or Firm — Norris McLaughlin, P.A.

(57) ABSTRACT

A photocurable composition is provided, which is characterized by comprising a polymerizable monomer component (A), an inorganic filler component (B) having an average particle diameter of 0.07 µm or more, an organic-inorganic composite filler component (C) comprising an inorganic filler component (C1) and an organic polymer component (C2) and having an average particle diameter of 0.5 µm or more, and a photopolymerization initiator (D), wherein the inorganic filler component (B) and the organic-inorganic composite filler component (C) are contained in a total amount of 100 to 1500 parts by mass relative to 100 parts by mass of the polymerizable monomer component (A), and the polymerizable monomer component (A), 90 parts by mass or more of the inorganic filler component (B) and 90 parts by mass or more of the organic-inorganic composite filler component (C) are selected in such a manner that specific requirements can be satisfied.

8 Claims, No Drawings

LIGHT CURABLE COMPOSITION

This application is a 371 application of PCT/JP2017/031244 filed Aug. 30, 2017, which claims foreign priority benefits under 35 U.S.C. § 119 of Japanese Application No. 2016-169468 filed Aug. 31, 2016, the disclosures of each of which are incorporated by reference herein in their entirety.

TECHNICAL FIELD

The present invention relates to a light curable composition, and specifically to a light curable composition used as a dental filling/restoring material for restoring a deep cavity formed in a posterior tooth.

BACKGROUND ART

Light curable compositions are rapidly spreading as dental filling/restoring materials and at present used in almost all treatments of front teeth because they impart color tones equivalent to those of natural teeth, and facilitate treatment. Also developed are those having a high mechanical strength which can be used for restoring of a posterior tooth subjected to high occlusal pressure.

As the dental filling/restoring materials, light curable compositions prepared by mixing a polymerizable monomer with large amounts of an inorganic filler and a photopolymerization initiator are advantageously used. For example, a dental adhesive material is applied to a cavity of a tooth to be restored, the cavity is filled with a filling/restoring material (light curable composition) and shaped into a tooth, and irradiated with active light using a special light irradiator for polymerization and curing, and the polymerized cured body thus formed restore the teeth. Alternatively, in a dental technician's office, a photocurable dental filling/restoring material is built up to the shape of the tooth to be restored on a plaster cast, the object is polymerized and cured by photoirradiation, subsequently in a dental clinic, the cured body of the dental filling/restoring material thus obtained is adhered to dentin with a dental cement, thereby restoring the tooth. When a dental filling/restoring material is used, its photocuring uses visible light in consideration of safety to human body, and thus a visible light photopolymerization initiator is usually used as the photopolymerization initiator.

In recent dental restoring, particularly regarded is the concept of minimal intervention, or the concept of maximizing the life of natural teeth by minimizing the amount of cutting of teeth. One of the factors behind the generalization of this concept is that the improvement of adhesion of a dental adhesive material to teeth allows treatment without excessive cutting of teeth. Against this backdrop, usefulness of a dental filling/restoring material (referred to as a composite resin) in clinical practices is increasingly growing.

With enlargement of the use range of composite resins, more attention is paid to simplification operations from the viewpoints of reduction of burdens on operators and patients, and reduction of technique sensitivity by operators. For example, for a dental adhesive material, a system with a simplified number of steps of treatment of the dental surface is developed.

In the restoration of a large cavity (for example, a cavity having a depth of 3 to 6 mm such as that formed in a posterior tooth) using a composite resin, usually used is a measure wherein a light curable composition to be a composite resin is applied to the cavity to a thickness of about 1 to 2 mm, and polymerized and cured by photoirradiation, and this operation is repeated. The reason for this is as follows; if a light curable composition is packed into a large cavity at a stroke and polymerized by photoirradiation, detachment tends to occur at the bottom or margin due to polymerization shrinkage and polymerization failure, which can cause coloring of the margin and subsequent failures such as secondary caries.

On the other hand, if a light curable composition is applied to a cavity little by little, and polymerized and cured every time for building up the composition, time and effort and necessary, and bubbles may be included in the interface between the layer polymerized and cured first and the layer polymerized and cured subsequently. If such inclusion of bubbles occurs, deterioration in the lifetime may be caused by the decrease of the strength of the polymerized cured body (composite resin), and secondary caries tends to occur.

In order to solve the above-described problems, Patent Literatures 1 to 4 propose light curable compositions causing less polymerization shrinkage (rate of shrinkage and shrinkage stress). These light curable compositions with low polymerization and shrinkage properties can be cured to their bottom and margin without gaps by a single time of photoirradiation within the range of the photocuring depth.

Additionally, Patent Literature 5 proposes a light curable composition wherein an inorganic filler is selected so as to satisfy the conditions that the refractive index (nF) of an inorganic oxide (inorganic filler) is between the value which is higher than the refractive index (nM) of a polymerizable monomer by 0.005, and lower than the refractive index (nP) of the polymer obtained by polymerizing the polymerizable monomer by 0.005. The light curable composition exhibits a deep curing depth, and accordingly, when such light curable composition is used for restoring of a deep cavity formed in a posterior tooth, for example, a single time of filling and photocuring achieves the restoring work.

However, the above-described prior art light curable compositions have improved properties in restoring of cavities, but have problems that the appearance of the cured body (composite resin) restoring the cavities are not harmonized with that of teeth.

Additionally, Patent Literature 6 proposes a dental filling/restoring material which satisfies the conditions that the refractive index (nM) of a polymerizable monomer before curing is between the value which is lower than the refractive index (nF) of an inorganic filler by 0.005 and the value which is higher than the refractive index (nF) of the inorganic filler by 0.005, and the refractive index (nP) of the polymerizable monomer after curing is between the value which is higher than the refractive index (nF) of the inorganic filler by 0.020 and higher than the refractive index (nF) of the inorganic filler by 0.040. This dental filling/restoring material has marked light permeability in the visible light region, and thus has a large curing depth, and its cured body has translucency close to that of natural teeth.

The above-described inventions achieved both of the largeness of curing depth and translucency close to that of natural teeth, but still require improvements from the viewpoint of harmony with natural teeth. Natural teeth have light diffusivity, so that dental filling/restoring materials must have light diffusivity to achieve sufficient harmony with natural teeth.

CITATION LIST

Patent Literature

Patent Literature 1: JP 2009-540107 A
Patent Literature 2: JP 2008-502697 A

Patent Literature 3: JP 2004-527602 A
Patent Literature 4: JP 2004-149587 A
Patent Literature 5: JP 62-86003 A
Patent Literature 6: WO 2014/050634 A

SUMMARY OF INVENTION

Technical Problem

Accordingly, the present invention is intended to provide a light curable composition useful as a dental filling/restoring material which achieves a deep curing depth and good workability in restoring of cavities, allow effective polymerization and curing to the bottom even in a deep cavity formed in a posterior tooth with a single time or a few times of filling followed by visible light irradiation, and the appearance including translucency and light diffusivity of the cured body thus formed is sufficiently harmonized with that of natural teeth.

Solution to Problem

The inventors carried out dedicated research for achieving the above-described aim. As a result of this, they found that the aim is achieved by adding an inorganic filler and an organic-inorganic composite filler to a light curable composition, the refraction indices of the inorganic filler and the organic-inorganic composite filler being in the range close to the refractive index of the polymerizable monomer, and are moderately apart from the refractive index of the polymer (cured body) obtained from the polymerizable monomer, and thus completed the present invention.

According to the present invention, provided is a light curable composition including: a polymerizable monomer component (A); an inorganic filler component (B) having an average particle size of 0.07 μm or more; an organic-inorganic composite filler component (C) including an inorganic filler component (C1) and an organic polymer component (C2) and having an average particle size of 0.5 μm or more; and a photopolymerization initiator (D), wherein the light curable composition includes the inorganic filler component (B) and the organic-inorganic composite filler component (C) in a total amount of 100 to 1500 parts by mass per 100 parts by mass of the polymerizable monomer component (A), and the polymerizable monomer component (A) and 90% by mass or more of the inorganic filler component (B) and 90% by mass or more of the organic-inorganic composite filler component (C) are selected so as to satisfy the conditions (X1) represented by the following formulae (1a-a to 1a-c), (1b-a to 1b-d), and (1c-a to 1c-b);

$$nF-0.015<nM<nF+0.015 \quad (1\text{a-a})$$

$$nPF-0.015<nM<nPF+0.015 \quad (1\text{a-b})$$

$$nPP-0.015<nM<nPP+0.015 \quad (1\text{a-c})$$

$$nF+0.005<nP<nF+0.050$$

or $$nF-0.050<nP<nF-0.005 \quad (1\text{b-a})$$

$$nPF+0.005<nP<nPF+0.050$$

or $$nPF-0.050<nP<nPF-0.005 \quad (1\text{b-b})$$

$$nPP+0.005<nP<nPP+0.050$$

or $$nPP-0.050<nP<nPP-0.005 \quad (1\text{b-c})$$

$$nPF-0.030<nPP<nPF-0.005 \quad (1\text{b-d})$$

$$nPF-0.020<nF<nPF+0.020 \quad (1\text{c-a})$$

$$nPP-0.020<nF<nPP+0.020 \quad (1\text{c-b})$$

(wherein
nM represents a refractive index of the polymerizable monomer component (A) at 25° C.,
nP represents a refractive index of a polymer obtained by polymerizing the polymerizable monomer component (A) at 25° C.,
nF represents a refractive index of the inorganic filler component (B) at 25° C.,
nPF represents a refractive index of the inorganic filler component (C1) in the organic-inorganic composite filler component (C) at 25° C., and
nPP represents a refractive index of the organic polymer component (C2) in the organic-inorganic composite filler component (C) at 25° C.)

The light curable composition of the present invention preferably satisfies the following requirements:

(1) The polymerizable monomer component (A), 90% by mass or more of the inorganic filler component (B), and 90% by mass or more of the organic-inorganic composite filler component (C) are selected so as to satisfy the conditions (X2) represented by the following formulae (2a-a to 2a-c), (2b-a to 2b-d), and (2c-a to 2c-b);

$$nF-0.010<nM<nF+0.010 \quad (2\text{a-a})$$

$$nPF-0.010<nM<nPF+0.010 \quad (2\text{a-b})$$

$$nPP-0.010<nM<nPP+0.010 \quad (2\text{a-c})$$

$$nF+0.010<nP<nF+0.040$$

or $$nF-0.040<nP<nF-0.010 \quad (2\text{b-a})$$

$$nPF+0.010<nP<nPF+0.040$$

or $$nPF-0.040<nP<nPF-0.010 \quad (2\text{b-b})$$

$$nPP+0.010<nP<nPP+0.040$$

or $$nPP-0.040<nP<nPP-0.010 \quad (2\text{b-c})$$

$$nPF-0.020<nPP<nPF-0.010 \quad (2\text{b-d})$$

$$nPF-0.015<nF<nPF+0.015 \quad (2\text{c-a})$$

$$nPP-0.015<nF<nPP+0.015 \quad (2\text{c-b})$$

(wherein
nM, nP, nF, nPP, and nPF have the same meanings as described above);

(2) a total amount of the polymerizable monomer component (A), the inorganic filler component (B), and the organic-inorganic composite filler component (C) satisfy the conditions (X1) or the conditions (X2);

(3) the polymerizable monomer component (A) includes a plurality of kinds of polyfunctional (meth)acryl compounds, and its refractive index (25° C.) is within the range of 1.48 to 1.55;

(4) the plurality of kinds of polyfunctional (meth)acryl compounds are composed of a combination of polyfunctional aromatic (meth)acrylates and polyfunctional aliphatic (meth)acrylates;

(5) the polyfunctional aromatic (meth)acrylate is 2,2-bis[(3-methacryloyloxy-2-hydroxypropyloxy)phenyl]propane and/or 2,2-bis[(4-methacryloyloxypolyethoxyphenyl)propane, and the polyfunctional aliphatic (meth)acrylate is triethylene glycol dimethacrylate and/or 1,6-bis(methacrylethyloxycarbonylamino)trimethylhexane;

(6) the organic-inorganic composite filler component (C) is an organic-inorganic composite filler including an aggregate prepared by agglutinating inorganic primary particles having an average particle size of 10 to 1000 nm, an organic resin phase which covers a surface of the inorganic primary particles and bonds together the inorganic primary particles, and aggregation gaps which are formed between the organic resin phases covering the surface of the inorganic primary particles, and have a pore volume (wherein the pore means those having a pore diameter of 1 to 500 nm) of 0.01 to 0.30 cm/g as measured by mercury porosimetry;

(7) the curing depth is 6 mm or more as measured by carrying out photoirradiation for 30 seconds using a halogen type dental light irradiator with a light quantity of 500 mW/cm$^2$;

(8) a contrast ratio measured in an uncured state with a thickness of 1 mm is 0.30 or less, and a contrast ratio measured in a cured body state with a thickness of 1 mm is 0.33 or more;

(9) a degree of diffusion D of a cured body having a thickness of 0.5 mm defined by the following formula is 15 or more, $$D=(((I(20)/\cos 20°)+(I(70)/\cos 70°))/(2 \times I(0))) \times 100$$

(wherein I(W/sr) represents the intensity of light passing through a sample, I(0), I(20), and I(70) represent intensity of light at angles of 0, 20, and 70, respectively, with respect to an incident direction of light);

(10) the light curable composition further includes a coloring agent (E), has a contrast ratio of 0.30 or less as measured in an uncured state having a thickness of 1 mm, and a contrast ratio of 0.55 or less as measured in a cured body state having a thickness of 1 mm;

(11) the light curable composition is a dental restoring filler including a light curable composition; and

(12) the dental restoring filler is used for restoring of a cavity formed in a posterior tooth.

In the present invention, the refractive index of the polymer obtained by polymerizing the polymerizable monomer component (A) means, as described in the below-described Examples, the value measured using an Abbe refractometer for a polymer having a thickness of 0.5 mm obtained by casting polymerization of the polymerizable monomer component (A) under predetermined conditions (almost the same as the polymerization conditions in a cavity). More specifically, when the kind of the polymerizable monomer component (A) is one, the value is the refractive index of the homopolymer of the polymerizable monomer, and when the kind of the polymerizable monomer component (A) is two or more, the value is the refractive index of the random copolymer of these plurality of kinds of polymerizable monomers. The polymerization conditions are established so as to be the same as the case where filling and restoring of the cavity formed in a teeth is carried out.

The refractive index means a value at 25° C. unless otherwise specified.

Advantageous Effects of Invention

When the light curable composition of the present invention is used as a dental filling/restoring material, it has high light permeability in the visible light region before curing, and thus has a deep curing depth. Accordingly, even for a deep cavity in a posterior tooth, a single time of filling and photopolymerization, or repetition of a small number of times of filling and photopolymerization allows restoring of a large cavity formed in a posterior tooth.

Additionally, the cured body of the light curable composition has translucency and light diffusivity close to those of natural teeth, and its appearance is harmonized with the appearance of natural teeth. Accordingly, when it is used as a dental filling/restoring material, it restores a cavity formed in a posterior tooth without impairing aesthetic appearance.

DESCRIPTION OF EMBODIMENTS

The light curable composition of the present invention used as a dental filling/restoring material is packed into a cavity formed in a tooth by caries or other reason, and photo-cured to restore the tooth. The light curable composition includes the polymerizable monomer component (A), the inorganic filler component (B) having an average particle size of 0.07 μm or more, the organic-inorganic composite filler component (C) having an average particle size of 0.5 μm or more, and the photopolymerization initiator (D) as essential components, also includes other components as needed in addition to these essential components, and the polymerizable monomer component (A), the inorganic filler component (B), and the organic-inorganic composite filler component (C) are selected so as to satisfy specific conditions.

Each component is described below in detail.

<Polymerizable Monomer Component (A)>

In the light curable composition of the present invention, the polymerizable monomer useful as this component is an organic compound having a polymerizable group and being polymerizable by a photopolymerization initiator. Particularly, the compound achieves high transparency and light transmittance of 85% or more, more preferably 90% or more of the polymer to be obtained.

Typical examples of the polymerizable monomer include cationic polymerizable monomers and radical polymerizable monomers.

Typical examples of the cationic polymerizable monomer include vinyl ether compounds, epoxy compounds, oxetane compounds, cyclic ether compounds, bicyclic orthoester compounds, cyclic acetal compounds, bicyclic acetal compounds, and cyclic carbonate compounds.

Typical examples of the radical polymerizable monomer include (meth)acrylic compounds.

In the present invention, (meth)acrylic compounds are preferred as the polymerizable monomer component (A) particularly from the viewpoint of low living body toxicity and high polymerization activity.

In the present invention, the (meth)acryl compounds are classified into monofunctional and bifunctional or higher polyfunctional ones (for example, bifunctional, trifunctional, and tetrafunctional ones), and examples of them include followings.

(A1) Monofunctional (meth)acryl compounds;
monofunctional methacryl compounds are classified into those having an acidic group and those having no acidic group.

(A1-1) Examples of monofunctional (meth)acryl compound having no acidic group;
methyl (meth)acrylate,
ethyl (meth)acrylate
n-butyl (meth)acrylate,
2-ethylhexyl (meth)acrylate,
n-lauryl (meth)acrylate,
n-stearyl (meth)acrylate,
tetrafurfuryl (meth)acrylate,
glycidyl (meth)acrylate,
methoxy ethylene glycol (meth)acrylate,
methoxy diethylene glycol (meth)acrylate,
methoxy-triethylene glycol (meth)acrylate,
methoxy polyethylene glycol (meth)acrylate,
ethoxyethylene glycol (meth)acrylate,
ethoxydiethylene glycol (meth)acrylate,
ethoxytriethylene glycol (meth)acrylate,
ethoxypolyethylene glycol (meth)acrylate,
phenoxyethylene glycol (meth)acrylate,
phenoxydiethylene glycol (meth)acrylate,
phenoxytriethylene glycol (meth)acrylate,
phenoxypolyethylene glycol (meth)acrylate,
cyclohexyl (meth)acrylate,
benzyl (meth)acrylate,
isoboronyl (meth)acrylate,
trifluoroethyl (meth)acrylate,
2-hydroxyethyl (meth)acrylate,
3-hydroxypropyl (meth)acrylate,
4-hydroxybutyl (meth)acrylate,
6-hydroxyhexyl (meth)acrylate,
10-hydroxydecyl (meth)acrylate,
propylene glycol mono(meth)acrylate,
glycerol mono(meth)acrylate,
erythritol mono(meth)acrylate,
N-methylol (meth)acrylamide,
N-hydroxyethyl (meth)acrylamide, and
N,N-(dihydroxyethyl) (meth)acrylamide.

(A1-2) Examples of monofunctional (meth)acryl compound having acidic group;
(meth)acrylic acid,
N-(meth)acryloyl glycine,
N-(meth)acryloyl aspartic acid,
N-(meth)acryloyl-5-aminosalicylic acid,
2-(meth)acryloyl oxyethyl hydrogen succinate,
2-(meth)acryloyl oxyethyl hydrogen phthalate,
2-(meth)acryloyl oxyethyl hydrogen maleate,
6-(meth)acryloyl oxyethyl naphthalene-1,2,6-tricarboxylic acid,
O-(meth)acryloyl tyrosine,
N-(meth)acryloyl tyrosine,
N-(meth)acryloyl phenylalanine,
N-(meth)acryloyl-p-aminobenzoic acid,
N-(meth)acryloyl-o-aminobenzoic acid,
p-vinylbenzoic acid,
2-(meth)acryloyloxybenzoic acid,
3-(meth)acryloyloxybenzoic acid,
4-(meth)acryloyloxybenzoic acid,
N-(meth)acryloyl-5-aminosalicylic acid,
N-(meth)acryloyl-4-aminosalicylic acid,
Acid anhydrides corresponding to the above-described carboxylic compounds,
11-(meth)acryloyloxyundecane-1,1-dicarboxylic acid,
10-(meth)acryloyloxydecane-1,1-dicarboxylic acid,
12-(meth)acryloyl oxide decane-1,1-dicarboxylic acid,
6-(meth)acryloyloxyhexane-1,1-dicarboxylic acid,
2-(meth)acryloyloxyethyl-3'-methacryloyloxy-2'-(3,4-dicarboxybenzoyloxy)propyl succinate,
4-(2-(meth)acryloyloxyethyl) trimellitate anhydride,
4-(2-(meth)acryloyloxyethyl) trimellitate,
4-(meth)acryloyl oxyethyl trimellitate,
4-(meth)acryloyloxybutyl trimellitate,
4-(meth)acryloyloxyhexyl trimellitate,
4-(meth)acryloyloxydecyl trimellitate,
4-(meth)acryloyloxybutyl trimellitate,
6-(meth)acryloyloxyethyl naphthalene-1,2,6-tricarboxylic anhydride,
6-(meth)acryloyloxyethylnaphthalene-2,3,6-tricarboxylic anhydride,
4-(meth)acryloyloxyethyl carbonyl propionoyl-1,8-naphthalic acid anhydride,
4-(meth)acryloyloxyethyl naphthalene-1,8-tricarboxylic anhydride,
9-(meth)acryloyloxynonane-1,1-dicarboxylic acid,
13-(meth)acryloyloxytridecane-1,1-dicarboxylic acid,
11-(meth)acrylamideundecane-1,1-dicarboxylic acid,
2-(meth)acryloyloxyethyl dihydrogenphosphate,
2-(meth)acryloyloxyethyl phenylhydrogen phosphate,
10-(meth)acryloyloxydecyl dihydrogen phosphate,
6-(meth)acryloyloxyhexyl dihydrogen phosphate,
2-(meth)acryloyloxyethyl-2-bromoethyl hydrogenphosphate,
2-(meth)acrylamide ethyldihydrogenphosphate,
2-(meth)acrylamide-2-methylpropanesulfonic acid
10-sulfodecyl (meth)acrylate,
3-(meth)acryloxypropyl-3-phosphonopropionate,
3-(meth)acryloxypropyl phosphonoacetate,
4-(meth)acryloxybutyl-3-phosphonopropionate,
4-(meth)acryloxybutyl phosphonoacetate,
5-(meth)acryloxypentyl-3-phosphonopropionate,
5-(meth)acryloxypentyl phosphonoacetate,
6-(meth)acryloxyhexyl-3-phosphonopropionate,
6-(meth)acryloxyhexyl phosphonoacetate,
10-(meth)acryloxydecyl-3-phosphonopropionate,
10-(meth)acryloxydecyl phosphonoacetate,
2-(meth)acryloxyethyl-phenyl phosphonate,
2-(meth)acryloyloxyethyl phosphonic acid,
10-(meth)acryloyloxydecyl phosphonic acid,
N-(meth)acryloyl-ω-aminopropyl phosphonic acid,
2-(meth)acryloyloxyethylphenylhydrogen phosphate,
2-(meth)acryloyloxyethyl-2'-bromoethylhydrogen phosphate, and
2-(meth)acryloyloxyethyl phenylphosphonate.

(A2) Bifunctional (meth)acryl compound;
Bifunctional (meth)acryl compounds are broadly classified into those having an aromatic group and aliphatic ones having no aromatic group.

(A2-1) Examples of aromatic bifunctional (meth)acryl compound;
2,2-bis(methacryloyloxyphenyl)propane,
2,2-bis(methacryloylethoxyphenyl)propane,
2,2-bis[4-(3-methacryloyloxy)-2-hydroxypropoxyphenyl] pro pane,
2,2-bis(4-methacryloyloxyphenyl)propane,
2,2-bis(4-methacryloyloxypolyethoxyphenyl)propane,
2,2-bis(4-methacryloyloxydiethoxyphenyl)propane,
2,2-bis(4-methacryloyloxytetraethoxyphenyl)propane,
2,2-bis(4-methacryloyloxypentaethoxyphenyl)propane,
2,2-bis(4-methacryloyloxydipropoxyphenyl)propane,
2-(4-methacryloyloxydiethoxyphenyl)-2(4-methacryloyloxydiethoxyphenyl)propane, 2-(4-methacryloyloxydiethoxyphenyl)-2(4-methacryloyloxytriethoxyphenyl)propane,
2-(4-methacryloyloxydipropoxyphenyl)-2-(4-methacryloyloxytriethoxyphenyl)propane,
2,2-bis(4-methacryloyloxypropoxyphenyl)propane,
2,2-bis(4-methacryloyloxyisopropoxyphenyl) propane,
acryl compounds corresponding to the above-described various methacryl compounds, and
diadducts obtained by adding a methacrylate or acrylate having an OH group to a diisocyanate compound having an aromatic group.

Typical examples of the methacrylate having an OH group include 2-hydroxyethyl methacrylate, 2-hydroxypropyl methacrylate, and 3-chloro-2-hydroxypropyl methacrylate, and typical examples of the diisocyanate include diisocyanate methylbenzene and 4,4'-diphenylmethane diisocyanate.

(A2-2) Examples of aliphatic bifunctional (meth)acryl compound;
ethylene glycol dimethacrylate,
diethylene glycol dimethacrylate,
triethylene glycol dimethacrylate,
tetraethylene glycol dimethacrylate,
neopentyl glycol dimethacrylate,
1,3-butanediol dimethacrylate,
1,4-butanediol dimethacrylate,
1,6-hexanediol dimethacrylate,
1,2-bis(3-methacryloyloxy-2-hydroxypropoxy)ethyl,
1,6-bis(methacrylethyloxycarbonylamino)trimethylhexane,
acrylates corresponding to the above-described various methacrylates, and
diadducts obtained by adding a methacrylate or acrylate having an OH group to an aliphatic diisocyanate compound.

Typical examples of the aliphatic diisocyanate include hexamethylene diisocyanate, trimethylhexamethylene diisocyanate, diisocyanate methylcyclohexane, isophorone diisocyanate, and methylene bis(4-cyclohexyl isocyanate), and examples of the methacrylate having an OH group include 2-hydroxyethyl methacrylate, 2-hydroxypropyl methacrylate, and 3-chloro-2-hydroxypropyl methacrylate.

The above-described compounds are examples of those containing no acidic group, and those containing an acidic group include the following ones;
1,2-bis(3-methacryloyloxy-2-hydroxypropoxy)ethyl,
di(2-methacryloyloxypropyl) phosphate,
di[2-(meth)acryloyloxyethyl] hydrogen phosphate,
di[4-(meth)acryloyloxybutyl] hydrogen phosphate,
di[6-(meth)acryloyloxyhexyl] hydrogen phosphate,
di[8-(meth)acryloyloxyoctyl] hydrogen phosphate,
di[9-(meth)acryloyloxynonyl] hydrogen phosphate,
di[10-(meth)acryloyloxydecyl] hydrogen phosphate, and
1,3-di(meth)acryloyloxypropyl-2-dihydrogen phosphate.
(A3) Trifunctional (meth)acryl compound;
trimethylolpropane tri(meth)acrylate,
trimethylolethane tri(meth)acrylate,
pentaerythritol tri(meth)acrylate,
dipentaerythritol tri(meth)acrylate,
ethoxylated trimethylolpropane tri(meth)acrylate,
propoxylated trimethylolpropane tri(meth)acrylate, and
tris(2-(meth)acryloxyethyl isocyanurate).
(A4) Tetrafunctional (meth)acryl compound;
pentaerythritol tetra(meth)acrylate,
ethoxylated pentaerythritol tetra(meth)acrylate,
propoxylated pentaerythritol tetra(meth)acrylate, and
ethoxylated ditrimethylolpropane tetra(meth)acrylate.

In the present invention, at least one of the above-described various polymerizable monomers is selected, and used as the polymerizable monomer component (A) so as to satisfy the below-described conditions (X1). In this case, the use of a plurality of kinds polyfunctional polymerizable monomers containing at least two polymerizable groups (for example, the above-described polyfunctional (meth)acryl compound) is preferred for improving mechanical properties (for example, strength and water resistance) of the cured body to be formed and its adhesion to dentin. More specifically, even if a polymerizable monomer is selected so as to satisfy the below-described conditions (X1), if the polymerizable monomers to be used are only monofunctional ones, the cured body to be formed has low mechanical strength and achieves insufficient performance as a restoring material.

Usually, the polyfunctional polymerizable monomer is preferably used in the proportion of 60% by mass or more, particularly preferably 70% by mass or more of the polymerizable monomer component (A).

In the present invention, other than the above-described various polymerizable monomers, for example, polymerizable monomers having photocleaving properties such as those disclosed in JP 2009-540107 A and WO 2007/146239 A, or the polymerizable macrocyclic oligomers disclosed in JP 2008-502697 A may also be used. These polymerizable monomers are particularly effective for suppression of polymerization shrinkage.

<Inorganic Filler Component (B)>

The inorganic filler component (B) may be selected from various inorganic fillers which are known in the field of dental curable compositions as long as they satisfy the below-described conditions (X1), but its average particle size must be 0.07 μm or more. The reason is that those having an average particle size of less than 0.07 μm are transparent regardless of their refractive index because their particle size is smaller than the wavelength of visible light, which makes it impossible to obtain a cured body having a desired appearance harmonized with natural teeth. The average particle size of the inorganic filler is preferably 0.1 μm or more from the viewpoint of ensuring mechanical physical properties of the cured body to be obtained.

Additionally, the average particle size is preferably 5 μm or less, and particularly preferably 3 μm or less, and most preferably 1 μm or less from the viewpoint of uniformly dispersing the inorganic filler in the curable composition, achieving high surface lubricity of the cured body to be obtained, and ensuring its aesthetic appearance.

The average particle size of the inorganic filler means a value of median diameter represented by the volume fraction measured using a particle size analyzer based on the principle of a laser diffraction scattering method and others.

Typical examples of the inorganic filler include base metals, semimetals, transition metals, their oxides, composite oxides, halides, sulfates, and their double salts, and their mixtures may be used as an inorganic filler. Preferably, oxides and composite oxides of metals such as silicon, titanium, aluminum, zirconium, and tin are used. These metallic composite oxides may further include alkali metals and alkaline earth metals such as sodium, potassium, magnesium, and calcium.

The particle shape of the inorganic filler is not particularly limited, but is preferably generally spherical or spherical, and more preferably spherical for achieving high surface lubricity of the cured body and securing aesthetic appearance. In the present description, generally spherical refers to those having an average uniformity is 0.5 or more, and those having an average uniformity of 0.6 or more are particularly referred to as spherical.

In the present invention, particularly preferred inorganic fillers are silica; composite oxides including silicon as a constitutional element; clay minerals or silicates (hereinafter they are referred to as silica-based fillers). These silica-based fillers have marked chemical stability, and easily surface-treated with a silane coupling agent or the like.

Specific examples of the silica-based filler are as follows.

Silica such as quartz, precipitated silica, fumed silica, and sol-gel silica;

composite oxides including silicon as a constitutional element such as silica-titania, silica-zirconia, silica-barium oxide, silica-lanthania, silica-alumina, silica-calcia, silica-strontium oxide, silica-magnesia, silica-titania-sodium oxide, silica-titania-potassium oxide, silica-zirconia-sodium oxide, silica-zirconia-potassium oxide, silica-alumina-sodium oxide, and silica-alumina-potassium oxide;

clay minerals or silicates such as talc, montmorillonite, zeolite, and calcium silicate.

Oxides and fluorides of lanthanoid and yttrium such as ytterbium fluoride and yttrium fluoride are al so preferred because they provide good X ray contrast.

Additionally, cation-eluting inorganic fillers such as silicate glass and fluoroaluminosilicate glass may also be used.

In the present invention, silica composite oxides such as silica-zirconia and silica-titania are most preferred as the inorganic filler of the inorganic filler component (B) because they provide good X-ray contrast, adjust the refractive index according to the silica content, and easily satisfy specific conditions.

Furthermore, the inorganic filler component (B) after being subjected to surface treatment with a surface treatment agent such as a silane coupling agent improves conformity with a polymerizable monomer, and improves mechanical strength and water resistance of the cured body to be obtained. Examples of the silane coupling agent include the following ones;
methyltrimethoxysilane,
methyltriethoxysilane,
methyltrichlorosilane,
dimethyldichlorosilane,
trimethylchlorosilane,
vinyltrichlorosilane,
vinyltriethoxysilane,
vinyltris(β-methoxyethoxy)silane,
γ-methacryloyloxypropyltrimethoxysilane,
γ-chloropropyltrimethoxysilane,
γ-glycidoxypropyltrimethoxysilane, and
hexamethyldisilazane.

<Organic-Inorganic Composite Filler Component (C)>

In the present invention, the organic-inorganic composite filler component (C) include the inorganic filler component (C1) and the organic polymer component (C2).

The organic-inorganic composite filler component (C) may be selected from known various organic-inorganic composite fillers as long as they satisfy the below-described conditions (X1).

The average particle size of the organic-inorganic composite filler must be 0.5 μm or more, more preferably 3.0 μm or more, and most preferably 5.0 μm or more, from the viewpoints of achieving high light diffusivity and securing aesthetic appearance of the cured body to be obtained.

On the other hand, if the average particle size of the organic-inorganic composite filler component (C) is too large, the surface area per unit mass decreases, and mechanical strength of the cured body decreases. From these viewpoints, the average particle size of the organic-inorganic composite filler component (C) is preferably 50 μm or less, particularly preferably 30 μm or less, and most preferably 20 μm or less.

Typical examples of the organic-inorganic composite filler component (C) described above include an organic-inorganic composite filler prepared by complexing the polymerizable monomers useful as the polymerizable monomer component (A) exemplified above and the inorganic fillers useful as the inorganic filler component (B). More specifically, it is an organic-inorganic composite filler including a polymer of the polymerizable monomer component (A) as the organic polymer component (C2) and the inorganic filler component (B) as the inorganic filler component (C1). The polymerizable monomer useful for obtaining the organic polymer component (C2) and the inorganic filler useful as the inorganic filler component (C1) are preferably those listed as the preferred polymerizable monomer of the polymerizable monomer component (A) and the preferred inorganic filler of the inorganic filler component (B), respectively.

In the present invention, the organic-inorganic composite filler component (C) may be used regardless of the manufacturing method or the presence or absence of pores, and, from the viewpoint of mechanical strength of the cured body, is preferably the organic-inorganic composite filler described in WO 2013/039169 A wherein the surface of the agglomerated particles is covered by an organic polymer and has pores.

For the pores, the volume of the micropores formed between the organic resin phases preferably include aggregation gaps of 0.01 to 0.30 cm$^3$/g in the volume measurement of fine pores with a pore diameter of 1 to 500 nm as measured by mercury porosimetry.

In order to form the preferred pores, the inorganic filler in the organic-inorganic composite filler preferably has a primary particle size of 10 to 1000 nm.

The shape of the organic-inorganic composite filler is not particularly limited; generally spherical or spherical one is preferred, and spherical one is more preferred, from the viewpoint of relaxation of polymerization shrinkage stress.

The shape (average uniformity) of the inorganic filler and the organic-inorganic composite filler is measured using a scanning or transmission electron microscope. Specifically, the average uniformity is determined from the maximum length and the minimum width of the inorganic filler and the organic-inorganic composite filler, which are obtained by image analysis images of the inorganic filler and the organic-inorganic composite filler. The images shot by an electron microscope are selected from those having a clear contrast and allows discrimination of the contours of particles.

The image analysis is carried out using an image analysis software which can measure at least the maximum length and the minimum width of particles. Randomly selected 100 particles are measured for the maximum length and the minimum width of the particles by the above-described method, and the average uniformity of the particles is calculated by the following formula.

$$\text{Average uniformity} = \frac{\sum_{i=1}^{n} Bi/Li}{n} \quad \text{[Mathematical Formula 1]}$$

In the above formula, the number of particles is defined as (n), the maximum length of the particle of the number (i) is defined as the major axis (Li), and the diameter in a direction orthogonal to the major axis is defined as the minimum width (Bi).

The mass ratio between the inorganic filler component (C1) and the organic polymer (C2) in the organic-inorganic composite filler component (C) is not particularly limited, but from the viewpoints of mechanical strength of the organic-inorganic composite filler and mechanical strength of the cured body, the inorganic filler component (C1):the organic polymer (C2) is preferably in the range of 70:30 to 95:5, particularly preferably in the range of 75:25 to 93:7, and most preferably in the range of 80:20 to 90:10.

When the weight ratio between the inorganic filler component (C1) and the organic polymer (C2) is outside the above-described range and the amount of the inorganic filler component (C1) is too much, the organic polymer (C2) is deficient, bonding between the inorganic filler components (C1) is insufficient, and mechanical strength decreases. On the other hand, if the amount of the inorganic filler component (C1) is too small, the organic polymer (C2) having poor mechanical strength to the inorganic filler component (C1) increases, so that the mechanical strength decreases.

The inorganic filler component (B) and the organic-inorganic composite filler component (C) are used in a total amount of 100 to 1500 parts by mass, preferably 150 to 1000 parts by mass, and most preferably 170 to 600 parts with reference to 100 parts by mass of the polymerizable monomer component (A), thereby making the viscosity of the light curable composition in the range suitable to filling operation for a cavity, suppressing polymerization shrinkage during curing, and achieving good mechanical properties of the cured body to be obtained. More specifically, if the amounts of usage of the inorganic filler component (B) and the organic-inorganic composite filler component (C) are too small, polymerization shrinkage during curing heavily occurs, and the cured body has poor mechanical properties. Furthermore, if the usages of the inorganic filler component (B) and the organic-inorganic composite filler component (C) are too much, the viscosity of the light curable composition can be excessively high, which makes it difficult to fill a cavity.

Furthermore, from the viewpoint of the cured body strength of the light curable composition, the content of the inorganic filler component (B) must be not less than a certain amount, while from the viewpoint of imparting light diffusivity, the content of the organic-inorganic composite filler component (C) must be not less than a certain amount. Accordingly, the mixing ratio (mass) between the inorganic filler component (B) and the organic-inorganic composite filler component (C) is from 9:1 to 1:9, preferably from 7:3 to 2:8, and most preferably 6:4 to 3:7.

<Selection of Polymerizable Monomer Component (A), Inorganic Filler Component (B), and Organic-Inorganic Composite Filler Component (C)>

In the present invention, the polymerizable monomer component (A), 90% by mass or more of the inorganic filler component (B), and 90% by mass or more of the organic-inorganic composite filler component (C) must be selected so as to satisfy the conditions (X1) represented by the following formulae (1a-a to 1a-c), (1b-a to 1b-d), and (1c-a to 1c-b);

$$nF-0.015<nM<nF+0.015 \quad (1a\text{-}a)$$

$$nPF-0.015<nM<nPF+0.015 \quad (1a\text{-}b)$$

$$nPP-0.015<nM<nPP+0.015 \quad (1a\text{-}c)$$

$$nF+0.005<nP<nF+0.050$$

or $$nF-0.050<nP<nF-0.005 \quad (1b\text{-}a)$$

$$nPF+0.005<nP<nPF+0.050$$

or $$nPF-0.050<nP<nPF-0.005 \quad (1b\text{-}b)$$

$$nPP+0.005<nP<nPP+0.050$$

or $$nPP-0.050<nP<nPP-0.005 \quad (1b\text{-}c)$$

$$nPF+0.005<nPP<nPF+0.030$$

or $$nPF-0.030<nPP<nPF-0.005 \quad (1b\text{-}d)$$

$$nPF-0.020<nF<nPF+0.020 \quad (1c\text{-}a)$$

$$nPP-0.020<nF<nPP+0.020 \quad (1c\text{-}b)$$

(wherein nM represents the refractive index of the polymerizable monomer component (A) at 25° C., nP represents the refractive index of the polymer obtained by polymerizing the polymerizable monomer component (A) at 25° C., nF represents the refractive index of the inorganic filler component (B) at 25° C., nPF represents the refractive index of the inorganic filler component (C1) in the organic-inorganic composite filler component (C) at 25° C., and nPP represents the refractive index of the organic polymer component (C2) in the organic-inorganic composite filler component (C) at 25° C.)

Furthermore, they are preferably selected so as to satisfy the conditions (X2) represented by the following formula (2a-a to 2a-c), (2b-a to 2b-d) and (2c-a to 2c-b);

$$nF-0.010<nM<nF+0.010 \quad (2a\text{-}a)$$

$$nPF-0.010<nM<nPF+0.010 \quad (2a\text{-}b)$$

$$nPP-0.010<nM<nPP+0.010 \quad (2a\text{-}c)$$

$$nF+0.010<nP<nF+0.040$$

or $$nF-0.040<nP<nF-0.010 \quad (2b\text{-}a)$$

$$nPF+0.010<nP<nPF+0.040$$

or $$nPF-0.040<nP<nPF-0.010 \quad (2b\text{-}b)$$

$$nPP+0.010<nP<nPP+0.040$$

or $$nPP-0.040<nP<nPP-0.010 \quad (2b\text{-}c)$$

$$nPF+0.010<nPP<nPF+0.020$$

or $$nPF-0.020 < nPP < nPF-0.010 \quad (2\text{b-d})$$

$$nPF-0.015 < nF < nPF+0.015 \quad (2\text{c-a})$$

$$nPP-0.015 < nF < nPP+0.015 \quad (2\text{c-b})$$

(wherein nM, nP, nF, nPP, and nPF have the same meanings as described above).

More specifically, in the present invention, on the basis of the fact that the refractive index of the polymerizable monomer is commonly increased by polymerization, the inorganic filler component (B), and the inorganic filler component (C1) and the organic polymer component (C2) in the organic-inorganic composite filler component (C) are selected so as to satisfy the following (i) to (iii). As a result of this, it was succeeded in securing easiness of filling and restoring operations, making the appearance of the cured body formed in a cavity close to that of natural teeth, keeping harmony with natural teeth, and preventing deterioration in aesthetic appearance by restoring of the cavity.

(i) The refractive index nF of the inorganic filler component (B), and the refractive index nPF of the inorganic filler component (C1) in the organic-inorganic composite filler component (C), and the refractive index nPP of the organic polymer component (C2) are in a region very close to the refractive index nM of the polymerizable monomer component (A) (the formulae (1a-a to 1a-c)).

(ii) the refractive index nP of the polymer obtained by polymerizing the polymerizable monomer component (A) under predetermined conditions is in a region moderately far from the refractive index nF of the inorganic filler component (B) and the refractive index nPF of the inorganic filler component (C1) in the organic-inorganic composite filler component (C), the refractive index nPP of the organic polymer component (C2) is in a region far from the refractive index nP of the polymer obtained by polymerizing the polymerizable monomer component (A) under predetermined conditions, and the refractive index nPF of the inorganic filler component (C1) in the organic-inorganic composite filler (C) is in a region moderately far from the refractive index nPP of the organic polymer component (C2) in the organic-inorganic composite filler (C) (the formulae (1b-a to 1b-d)).

(iii) the refractive index nF of the inorganic filler component (B) is in a region very close to the refractive index nPP of the organic polymer component (C2) in the organic-inorganic composite filler (C), and the refractive index nPF of the inorganic filler component (C1) in the organic-inorganic composite filler (C) is in a region very close to the refractive index nF of the inorganic filler component (B) (the formulae (1c-a to 1c-b)).

For example, the formulae (1a-a to 1a-c) in the conditions (X1) are converted to the following formulae, respectively.

$$-0.015 < nM-nF < 0.015 \quad (1\text{a-a'})$$

$$-0.015 < nM-nPF < 0.015 \quad (1\text{a-b'})$$

$$-0.015 < nM-nPP < 0.015 \quad (1\text{a-c'})$$

As understood from this, the formula (1a-a') represents that the refractive index nF of the inorganic filler component (B) to be used is in a range very close to the refractive index nM of the polymerizable monomer component (A); the formula (1a-b') represents that the refractive index nPF of the inorganic filler component (C1) in the organic-inorganic composite filler component (C) is in a range very close to the refractive index nM of the polymerizable monomer component (A); and the formula (1a-c') represents that the refractive index nPP of the organic polymer component (C2) in the organic-inorganic composite filler component (C) is in a range very close to the refractive index nM of the polymerizable monomer component (A). Therefore, in the light curable composition including the polymerizable monomer component (A), the inorganic filler component (B), and the organic-inorganic composite filler component (C), light diffuse reflection and dispersion are extremely small at the interface between the polymerizable monomer component (A) and the inorganic filler component (B), the interface between the polymerizable monomer component (A) and the inorganic filler component (C1) in the organic-inorganic composite filler component (C), and the interface between the polymerizable monomer component (A) and the organic polymer component (C2) in the organic-inorganic composite filler component (C), and as a result of this, high light permeability and a deep curing depth are achieved.

When the contrast ratio of a light curable composition measured in an uncured state having a thickness of 1 mm is used as an index of light permeability of the light curable composition, the contrast ratio of the light curable composition is preferably 0.30 or less, particularly preferably 0.28 or less, and most preferably 0.26 or less, thereby achieving a deep curing depth. In addition, clinically, in order to achieve sufficient curability even in a deep cavity in a posterior tooth, the curing depth is required to be double the depth of clinical filling. Specifically, in order to fill to a thickness of 3 mm or more, a curing depth of 6 mm or more is required. More preferably, in order to fill to a thickness of 4 mm or more, the curing depth is preferably 8 mm or more. In the present invention, the contrast ratio of the curable composition is made 0.30 or less, thereby achieving a curing depth of 6 mm or more, particularly 8 mm or more, and even more 10 mm or more as measured by photoirradiation for 30 seconds using a halogen type dental light irradiator with a light quantity of 500 mW/cm$^2$, and, for example, even for a deep cavity formed in a posterior tooth, its filling and restoring operation can be easily achieved in a short time. In other words, the packing of the light curable composition into the cavity and curing by photoirradiation carried out for each time of packing can be completed in a single time or a few times.

For example, if the refractive index nF of the inorganic filler component (B) is out of the range of the formula (1a-a), the curing depth decreases, and a deep cavity in a posterior tooth cannot be filled without repeatedly performing filling and curing operation on the cavity by photoirradiation, which extremely decrease the efficiency of the filling and restoring operation.

The formulae (1b-a to 1b-d) in the conditions (X1) are converted to the following formulae, respectively.

$$0.005 < |nP-nF| < 0.050 \quad (1\text{b-a'})$$

$$0.005 < |nP-nPF| < 0.050 \quad (1\text{b-b'})$$

$$0.005 < |nP-nPP| < 0.050 \quad (1\text{b-c'})$$

$$0.005 < |nPP-nPF| < 0.030 \quad (1\text{b-d'})$$

As understood from this, the formulae (1b-a to 1b-d) indicate that the refractive index nF of the inorganic filler component (B) and the refractive index nP of the polymer of the polymerizable monomer component (A) to be used, the refractive index nPF of the inorganic filler component (C1) in the organic-inorganic composite filler component (C) and the refractive index nP of the polymer of the polymerizable monomer component (A), the refractive index nPP of the organic polymer component (C2) in the organic-inorganic composite filler component (C) and the refractive index nP of the polymer of the polymerizable monomer component (A), and the refractive index nPF of the inorganic filler component (C1) in the organic-inorganic composite filler component (C) and the refractive index nPP of the organic polymer component (C2) are moderately apart from each other. More specifically, as described above, the polymer itself obtained from the polymerizable monomer component (A) has high light permeability, and the refractive index nP of this polymer and the refractive index nF of the inorganic filler component (B), the refractive index nPF of the inorganic filler component (C1) in the organic-inorganic composite filler component (C) and the refractive index nPP of the organic polymer component (C2) are moderately apart from each other. Therefore, in the cured body obtained from the light curable composition, the degrees of diffuse reflection and dispersion are high the interface between the polymer of the polymerizable monomer component (A) and the inorganic filler component (B), the interface between the polymer of the polymerizable monomer component (A) and the inorganic filler component (C1) in the organic-inorganic filler component (C), and the interface between the polymer of the polymerizable monomer component (A) and the organic polymer component (C2) in the organic-inorganic filler component (C). Additionally, the refractive index nPF of the inorganic filler component (C1) and the refractive index nPP of the organic polymer component (C2) in the organic-inorganic composite filler component (C) do not change between before and after polymerization of the polymerizable monomer component (A) (before and after curing of the light curable composition), so that the difference must achieve both of sufficient transparency before curing of the light curable composition and the degrees of diffuse reflection and dispersion in the interface between the inorganic filler component (C1) and the organic polymer component (C2) in the organic-inorganic composite filler component (C) after curing the light curable composition, and the inorganic filler component (C1) and the organic polymer component (C2) in the organic-inorganic composite filler component (C) are selected so as to satisfy the relationship of the formula (1b-d). As a result of this, the light curable composition before curing has transparency, while the cured body of the light curable composition is translucent and has light diffusivity, and its appearance is harmonized with that of natural teeth.

When the contrast ratio of a light curable composition measured in a cured body state having a thickness of 1 mm is used as an index of translucency of the cured body of the light curable composition, the contrast ratio of the cured body is preferably 0.33 or more, particularly preferably 0.35 or more, and most preferably 0.40 or more, thereby achieving good harmony of translucency with natural teeth. The higher the light diffusivity, the higher the effect of blurring the line between natural teeth and the restored object, and the better the harmony with natural teeth. When the degree of diffusion D defined by the following formula is used as the index of light diffusivity of the cured body of the light curable composition, in order to achieve good harmony of light diffusivity with natural teeth, the degree of diffusion D of the cured body is preferably 15 or more, particularly preferably 20 or more, and most preferably 25 or more. In the following formula, I(W/sr) represents the intensity of light passing through the sample, I(0), I(20), and I(70) represent the intensity of light at angles of 0, 20, and 70, respectively.

$$D=(((I(20)/\cos 20°)+(I(70)/\cos 70°))/(2\times I(0)))\times 100$$

For example, when the refractive index nF of the inorganic filler component (B) does not satisfy the conditions represented by the formula (1b-a), the difference in the refractive index is so small that the cured body to be obtained has high transparency, and its appearance does not match with natural teeth, and thus aesthetic appearance cannot be ensured. Alternatively, even if the difference in the refractive index is big and translucency of the cured body is ensured, the curing depth decreases, and easiness of filling and restoring operation is impaired.

The formulae (1c-a to 1c-b) in the conditions (X1) are converted the following formulae, respectively.

$$-0.020<nF-nPF<0.020 \qquad (1\text{c-a}')$$

$$-0.020<nF-nPP<0.020 \qquad (1\text{c-b}')$$

As understood from these facts, the formula (1c) indicates that the difference between the refractive index nF of the inorganic filler component (B) and the refractive index nPF of the inorganic filler component (C1) in the organic-inorganic composite filler component (C), and the difference between the refractive index nF of the inorganic filler component (B) and the refractive index nPP of the organic polymer component (C2) in the organic-inorganic composite filler component (C) are in a very close region. If these differences in the refractive index are excessively big, even if the formulae (1a-a to 1a-c) are satisfied, uncured portion of the curable composition can be opaque, and the curing depth may decrease. When the formulae (1c-a to 1c-b) are satisfied, these inconveniences are certainly avoided.

As the above-described polymerizable monomer component (A), usually, a plurality of kinds of polymerizable monomers are used, and the combination adjusts the mechanical properties (for example, strength and water resistance) of the cured body to be obtained and its adhesion to dentin to desirable ranges. For example, as described above, polyfunctional polymerizable monomers are used as 60% by mass or more, particularly 70% by mass or more of the component (A), the plurality kinds of polymerizable monomers are used as the polyfunctional polymerizable monomers, and those having an aliphatic group, those having an aromatic group, and those having an acidic group are commonly used in combination.

Thus, when a plurality of kinds of polymerizable monomers are used as the component (A), the refractive index nM of the component (A) is determined by measuring the polymerizable monomer component which is actually mixed according to the method described in below-described Examples, but the refractive index nM of the polymerizable monomer satisfies additivity, so that the refractive index nM of the component (A) can be determined by adding the refractive index of each polymerizable monomer according to the amount ratio.

Additionally, when a plurality of kinds of polymerizable monomers are used as the component (A), the refractive index nP of the polymer (more specifically copolymer) obtained from the component (A) is measured by actually carrying out polymerization according to the method described in below-described Examples. However, the polymerization conditions for obtaining the polymer for measuring the refractive index nP are almost the same as the polymerization conditions for packing the light curable composition into a cavity formed in a tooth and curing it, and these monomers are sufficiently polymerized to be cured bodies. Accordingly, the refractive index nP of this polymer (copolymer) also satisfies additivity to a degree as the refractive index nM of the polymerizable monomer, and the approximate value of the refractive index nP of the polymer obtained from the component (A) can be calculated by adding the refractive index measured for the polymer of each monomer according to the amount ratio, so that the recipe can be designed using these values.

The inorganic filler component (B) and the organic-inorganic composite filler component (C) may be a plurality of kinds of inorganic fillers and organic-inorganic composite fillers, respectively.

When a plurality of kinds of inorganic fillers and organic-inorganic composite fillers are used as the inorganic filler component (B) and the organic-inorganic composite filler component (C), and a plurality of kinds of inorganic fillers are used as the inorganic filler component (C1) of the organic-inorganic composite filler, if the difference in the refractive index between the inorganic fillers, between the inorganic filler components in the organic-inorganic composite filler, and between the organic polymer components in the organic-inorganic composite filler are excessively big, the uncured portion of the curable composition can be opaque, and the curing depth may decrease. In order to securely avoid these inconveniences, when a plurality of kinds of inorganic fillers or organic-inorganic composite fillers are used, in these components, 90% by mass or more must satisfy the conditions (X1). Preferably 95% by mass or more, and most preferably all the inorganic fillers or organic-inorganic composite fillers respectively satisfy the conditions (X1).

Additionally, the refractive index of the above-described various inorganic fillers vary to a degree with the surface treatment using a silane coupling agent or the like. Therefore, even when an inorganic filler having a known refractive index is used, when it is used after surface treatment, the refractive index of the actually surface-treated inorganic filler must be measured.

Furthermore, when the above-described cation-releasing filler is used as the inorganic filler, or as the inorganic filler in the organic-inorganic composite filler, the refractive index must be measured in a state where all the cations contained in the filler are released. More specifically, the filler is used in combination with an acid component such as a polymerizable monomer containing an acidic group such as a carboxylate group or a phosphate group, and improves mechanical properties of the cured body through polymerization in the presence of ion crosslinking formed by released cations. The release of ions varies the refractive index, and cations are released from the filler at the initiation of polymerization. Accordingly, when this cation-releasing filler is used, its refractive index must be measured after cations have been released.

In the present invention, as the polymerizable monomer component (A), a plurality of kinds of polymerizable monomers are commonly used for adjusting the physical properties (mechanical properties and adhesion to the dentin) of the cured body. At this time, the kind and amount of the polymerizable monomer are preferably established so as to make the refractive index nM of the component (A) in the range of preferably 1.46 to 1.60, more preferably 1.48 to 1.55. More specifically, when the refractive index nM is established in the range of 1.46 to 1.60, the refractive index nP of the polymer obtained from the polymerizable monomer component (A) can be established in the range of approximately 1.45 to 1.62, and when the refractive index nM is established in the range of 1.48 to 1.55, the refractive index nP of the polymer obtained from the polymerizable monomer component (A) can be established in the range of approximately 1.47 to 1.57. Accordingly, of the inorganic filler components (C1) in the inorganic filler component (B) and the organic-inorganic composite filler component (C), the refractive index of the silica-based filler, particularly silica-based composite oxide is in the range of about 1.46 to 1.56 according to the silica content. More specifically, when the refractive index of the polymerizable monomer component (A) is established in the above-described range, the inorganic filler component (B) and the inorganic filler components (C1) in the organic-inorganic composite filler component (C) can be easily selected so as to satisfy the conditions (X1). More specifically, a silica-based composite oxide (for example, silica titania or silica zirconia) containing an appropriate amount of silica is used.

Furthermore, in order to adjust the refractive index nM in the above-described range using a plurality of kinds of polymerizable monomers, commonly, it is preferred that all of the a plurality of kinds of polymerizable monomers be selected from bifunctional (meth)acryl compounds, thereby satisfying the conditions (X1), and achieving desired mechanical properties of the cured body as a dental filling/restoring material. For example, a trifunctional or higher functional polymerizable monomer can increase the strength of the cured body, but decreases the curing depth in comparison with a bifunctional polymerizable monomer. The reason for this is uncertain, but likely due to that crosslinking proceeds without stopping near the irradiated surface, which hinders light to reach the bottom. Furthermore, a monofunctional polymerizable monomer tends to decrease the strength of the cured body.

When a plurality of kinds of bifunctional (meth)acryl compounds are selected, it is particularly preferred that an aromatic bifunctional (meth)acryl compound and an aliphatic bifunctional (meth)acryl compound be combined. The use of an aromatic bifunctional (meth)acryl compound is advantageous for increasing the strength of a cured body, but the compound has a relatively high viscosity, and an aliphatic bifunctional (meth)acryl compound has a relatively low viscosity. Therefore, combination of them allows adjustment of the viscosity of the polymerizable monomer component, and provides a light curable composition which is easy to pack. Further, a bifunctional (meth)acryl compound having a functional group such as an acidic group is advantageous for increasing adhesion to dentin, and the compound may be added to the combination of the aromatic and aliphatic compounds.

In the combination of an aromatic bifunctional (meth)acryl compound and an aliphatic bifunctional (meth)acryl compound, commonly, the nM and nP of the aromatic bifunctional (meth)acryl compound are high, and the nM and nP of the aliphatic bifunctional (meth)acryl compound are low. Accordingly, the use of them allows establishment of the loading of these compounds, and adjustment of the refractive index nM and nP to fall within the above-described range.

In the present invention, particularly preferred examples of the bifunctional (meth)acryl compound used as the polymerizable monomer component (A) include the following ones.

Aromatic bifunctional (meth)acryl compound;
2,2-bis[(3-methacryloyloxy-2-hydroxypropyloxy)phenyl] pro pane
nM: 1.552 nP: 1.570
2,2-bis[(4-methacryloyloxypolyethoxyphenyl)propane
nM: 1.540
nP: 1.567
Aliphatic bifunctional (meth)acryl compound;
Triethylene glycol dimethacrylate
nM: 1.460
nP: 1.510
1,6-bis(methacrylethyloxycarbonylamino)trimethylhexane
nM: 1.483
nP: 1.509

<(D) Photopolymerization Initiator>

In the light curable composition of the present invention, the photopolymerization initiator (D) is a component for polymerizing and curing the polymerizable monomer component (A) by photoirradiation. The wavelength of light irradiated for the polymerization and curing is usually in the visible light region for safety reasons. Accordingly, the photopolymerization initiator used herein has an excitation absorption wavelength range, particularly excitation maximum absorption wavelength range in the visible light region from 380 to 500 nm (preferably 400 to 500 nm).

The photopolymerization initiator is selected from known ones according to the polymerization mechanism of the polymerizable monomer component (A) to be used. For example, a photoradical generator is used as a radical polymerizable monomer such as the above-described (meth) acryl compound. Additionally, a known photoacid generator is used for a cationic polymerizable one.

Specific examples of the photoradical generator include the followings.

α-diketones;

for example, camphor quinone and 1-phenyl-1,2-propane dione.

Bisacyl phosphine oxides;

for example, bis(2,4,6-trimethylbenzoyl)-phenylphosphine oxide and 2,4,6-trimethylbenzoyl diphenylphosphine oxide.

α-aminoalkylphenones;

for example, 2-benzyl-2-dimethylamino-1-(4-morpholinophenyl)-butanone-1 and 2-methyl-1-(4-methylthiophenyl)-2-morpholinopropane-1-one.

Titanocenes;

titanocene compounds such as bis(η5-2,4-cyclopentadien-1-yl)-bis(2,6-difluoro-3-(1H-pyrrole-1-yl)phenyl) titanium.

In the present invention, among the above-described photoradical generators, from the viewpoints of good polymerization activity and low toxicity to living body, α-diketones and bisacyl phosphine oxides are preferred, and camphor quinone and 2,4,6-trimethylbenzoyl diphenyl phosphine oxide are more preferred. The excitation maximum absorption wavelength of camphor quinone is 470 nm, and the excitation maximum absorption wavelength of 2,4,6-trimethylbenzoyl diphenyl phosphine oxide is 380 nm.

These photoradical generators used as polymerization initiators may be used singly, or in combination of a plurality of them as necessary.

The photopolymerization initiator may be used in a so-called effective amount, and specifically used in the proportion of 0.01 to 30 parts by mass, particularly 0.1 to 5 parts by mass per 100 parts by mass of the polymerizable monomer component (A). Furthermore, from the viewpoints of decreasing the influence of light transmission inhibition by the polymerization initiator itself, securing a high curing depth, and avoiding deterioration of aesthetic appearance by coloring of the cured body by the color of the polymerization initiator, it is most preferred that the photopolymerization initiator be used in the proportion of 0.1 to 1 parts by mass per 100 parts by mass of the polymerizable monomer component (A).

In addition to the photopolymerization initiator, a reducing compound may be added for promoting polymerization.

Typical examples of the reducing compound include aromatic tertiary amines, and specific examples thereof include, but not limited to, the followings.

4-dimethylaminobenzoate,
ethyl 4-dimethylaminobenzoate,
lauryl 4-dimethylaminobenzoate,
3-dimethylaminobenzoate,
ethyl 3-dimethylaminobenzoate,
dimethylamino-p-toluidine,
diethyl amino-p-toluidine, and
p-tolyldiethanolamine.

Among these aromatic tertiary amines, 4-dimethylaminobenzoate and 4-dimethylaminobenzoate ester are preferred.

The loading of the reducing compound depends on the kind of the polymerizable monomer component (A) and other component to be combined, but is usually in the range of 0.001 to 20 mol, particularly 0.005 to 10 mol per 1 mol of the photopolymerization initiator.

Examples of the photoacid generator used as the photopolymerization initiator include diaryl iodonium salt compounds, sulfonium salt compounds, sulfonate compounds, halomethyl-substituted S-triazine derivatives, and pyridinium salt compounds, and diaryl iodonium salt compounds and halomethyl-substituted S-triazine derivatives are preferred.

The photoacid generator may be combined with the above-described photoradical generator; for example, the photoacid generator may be used in an amount of 0.001 to 20 mol, particularly 0.005 to 10 mol per 1 mol of the photoradical generator.

<(E) Coloring Agent>

The light curable composition of the present invention may include the coloring agent (E) according to the desired color tone of the cured body. More specifically, the coloring agent (E) is appropriately used for controlling the color of the cured body to be formed by being embedded in a cavity so as to make a desired appearance (for example, a color tone of healthy natural teeth or a plain white color tone of whitentened teeth).

The coloring agent may be a pigment or a dye, and those having different colors may be appropriately combined for adjusting the cured body to a desired color tone.

The pigment is typically an inorganic pigment, and examples of the inorganic pigment include titanium oxide, zinc oxide, zirconium oxide, zinc sulfide, aluminum silicate, calcium silicate, carbon black, iron oxide, copper chromite black, oxidation chrome green, chrome green, violet, chrome yellow, lead chromate, lead molybdate, cadmium titanate, nickel titanium yellow, ultramarine blue, cobalt blue, bismuth vanadate, cadmium yellow, and cadmium red. In the present invention, the inorganic pigment also works as an inorganic filler. Accordingly, when an inorganic pigment is used, 90% by mass or more of the total amount of the inorganic pigment and the inorganic filler component (C) must satisfy the above-described conditions (X1). However, as will be described later, since the loading of the inorganic pigment is an extremely small amount, usually, 90% by mass or more of the total amount of the inorganic pigment and the inorganic filler component (C) satisfies the conditions (X1) as long as 90% by mass or more of the inorganic filler component (C) satisfies the conditions (X1).

Additionally, organic pigments such as monoazo pigments, diazo pigments, diazo condensed pigments, perylene pigments, and anthraquinone pigments may also be used.

Examples of the dye include red color dyes such as KAYASET RED G (manufactured by Nippon Kayaku Co., Ltd.) and KAYASET RED B (manufactured by Nippon Kayaku Co., Ltd.); yellow dyes such as KAYASET Yellow 2G and KAYASET Yellow GN; and blue color dyes such as KAYASET Blue N, KAYASET Blue G, and KAYASET Blue B. In consideration of stability of the color tone in a mouth, the use of a water-insoluble pigment is more preferred than a water-soluble dye.

The coloring agent blocks light, and naturally influences the curing depth of the light curable composition. In particular, a white pigment (for example, titanium oxide, zinc oxide, zirconium oxide, zinc sulfide, barium sulfate, or aluminum silicate) is often used as a coloring agent because the deep cavity after restoring is darkened and has lowered aesthetic appearance, but these white pigments have particularly high light blocking properties, and thus further decrease the curing depth.

On the other hand, the light curable composition of the present invention satisfies the conditions (X1), so that exhibits a high curing depth, and thus the influence of the decrease of the curing depth by the use of a coloring agent is small. More specifically, even if a coloring agent is added in a small amount for adjusting the color tone of the cured body, a sufficiently deep curing depth is maintained, and easiness of filling and restoring is good in restoring of a deep cavity. More specifically, in the present invention, curing operation through filling of the light curable composition into a large cavity and its photoirradiation can be carried out with one or a small number of times of operations even if a coloring agent is included, whereby decrease of easiness of filling and restoring operation is effectively avoided.

Additionally, the light curable composition of the present invention satisfies the conditions (X1), so that its cured body has appropriate translucency. Therefore, for example, even if a white pigment is not used (or its usage is small), its translucency ensures harmony between the cured body and natural teeth, and exhibits excellent aesthetic appearance. More specifically, elimination or reduction of the usage of a white pigment contributes suppression of the decrease of the curing depth by a coloring agent.

In this manner, in the present invention, the decrease of the curing depth by using the coloring agent can be suppressed, but the degree of suppression is limited. Therefore, the loading of the coloring agent must be not higher than a predetermined amount. Usually, in order to ensure the curing depth suitable for filling and restoring of a deep cavity formed in a posterior tooth, the loading of a coloring agent is preferably limited to an amount which makes the contrast ratio of the dental filling/restoring material 0.30 or less, particularly 0.27 or less as measured at a thickness of 1 mm, and the loading of a coloring agent is preferably 80 ppm or less.

The contrast ratio is a scale of transparency determined from the impulse value Y obtained by a color-difference meter, and represented by the ratio of the Y value (Yb) on a black background to the Y value (Yw) on a white background (Yb/Yw). More specifically, when the contrast ratio is higher than the above-described range, the loading of the coloring agent is too much, the curing depth of the light curable composition decreases, and easiness of filling and restoring operations deteriorates.

Additionally, in the light curable composition, the loading of a coloring agent is preferably adjusted so as to make the contrast ratio 0.55 or less, particularly in the range of 0.35 to 0.53 as measured in a cured body state having a thickness of 1 mm, and the loading of a coloring agent is preferably approximately 0.001 ppm or more. More specifically, the contrast ratio of a standard natural tooth (enamel of a front tooth on the lip side) is said about 0.45 (Dider Diets chi, DMD, PhD, A New shading concept based on natural tooth color applied to direct composite restorations, Quintessence Int. 2006; 37: 91-102). The closer the contrast ratio of the cured body of the light curable composition to the contrast ratio of natural teeth, the higher harmony with the appearance of natural teeth is achieved. For example, if the contrast ratio of the cured body of the light curable composition is higher than the above-described range, the cured body embedded in a cavity (the point of a teeth to be restored) has too high opacity, and may look unnaturally white in comparison with surrounding natural teeth. On the other hand, if the contrast ratio of the cured body is too low, surrounding natural teeth look white while the cured body looks dark, whereby harmony of the appearance with surrounding may be destroyed.

Thus, in the present invention, the coloring agent is preferably added in an amount which makes the contrast ratio of the light curable composition (uncured product) 0.20 to 0.35, and the contrast ratio of the cured body of the light curable composition within the range of 0.40 to 0.70, and the loading of the coloring agent satisfying the range of the contrast ratio is commonly 0.001 to 80 ppm, particularly 0.01 to 60 ppm, and optimally in the range of 0.05 to 40 ppm, per the light curable composition.

In the present invention, when a pigment is used as a coloring agent, the average particle size of the pigment is usually about 1 μm or less. As necessary, a commercially available pigment may be adjusted to a smaller particle size by fine grinding. Additionally, in order to facilitate mixing with other component, a pigment may be added to the compound in the form of a dispersion. For example, it may be used in the form of a master batch prepared by dispersing a pigment in a low viscosity liquid such as a reactive diluent, or in a powder such as inorganic particles.

<Other Component>

The light curable composition of the present invention may include other known additive besides the components (A) to (E), within the range which will not impair the curing depth or aesthetic appearance.

For example, a polymerization inhibitor, an ultraviolet absorber, and a viscosity regulator may be added as necessary.

When any of them is added, its loading is preferably adjusted so as to make the contrast ratio of the light curable composition in the form of a cured body with a thickness of 1 mm 0.55 or less, particularly in the range of 0.35 to 0.53.

As a viscosity regulator, for example, a fine filler having a particle size of less than 0.07 μm, particularly in the range of 0.05 to 0.05 μm may be used. The loading of the fine filler is preferably 10 parts by mass or less, particularly 5 parts by mass or less per 100 parts by mass of the total amount of the inorganic filler component (B) and the organic-inorganic composite filler component (C), so as not to impair the above-described mechanical strength and surface lubricity.

The above-described light curable composition of the present invention is commonly obtained by thoroughly mixing the above-described essential components and optional components in predetermined amounts, and as necessary subjecting the paste thus obtained to defoaming under reduced pressure to remove bubbles.

The light curable composition of the present invention is useful as a dental filling/restoring material, and can be used for restoring of any teeth. In particular, it is suitable for restoring of a cavity formed in a posterior tooth, and is used in the same manner as a general usage of a known composite resin filling.

For example, after the cavity of a posterior tooth to be restored is treated with an appropriate pretreatment material or adhesion material, the light curable composition of the present invention is packed into the cavity, formed into a teeth shape, and then irradiated with strong light using a special light irradiator, thereby achieving polymerization and curing. More specifically, even if the cavity formed in the posterior tooth is large, restoring can be achieved with a single time or a few times of filling and curing, which is particularly suitable for restoring of a deep cavity of primary or secondary grade. Furthermore, the composition is optimum for restoring of a deep cavity with a depth of 3 to 6 mm. For these deep cavities, restoring can be completed with a single time of polymerization, or a few times of repetition of filling and photopolymerization.

The cured body obtained by curing the light curable composition of the present invention preferably has a bending strength of 100 Mpa or more, more preferably 110 Mpa or more, and particularly preferably 120 Mpa or more as measured by the below-described method. The bending strength can be improved by increasing the average uniformity of the inorganic filler component (B) and the organic-inorganic composite filler component (C) included in the light curable composition of the present invention. In particular, the bending strength can be improved by increasing the average uniformity of the organic-inorganic composite filler component (C). More specifically, the use of a generally spherical or spherical inorganic filler or an organic-inorganic composite filler avoids stress concentration in a cured body obtained by curing a light curable composition.

The cured body obtained by curing the light curable composition of the present invention preferably has a shrinkage stress of 1.3 Mpa or less, more preferably 1.0 Mpa or less, and particularly preferably 0.9 Mpa or less as measured by the below-described method.

EXAMPLES

The present invention is further specifically described below with reference to examples, but the present invention will not be limited to these examples.

In the following examples and comparative examples, refractive index nM of a polymerizable monomer (or the polymerizable monomer component (A) including a plurality of kinds of polymerizable monomers) at 25° C., the refractive index nP of the polymer obtained by polymerizing the polymerizable monomer (or the polymerizable monomer component (A)) at 25° C., the refractive index nPP of the organic polymer in the organic-inorganic composite filler, the refractive index nF of the inorganic filler at 25° C., and the refractive index nPF of the inorganic filler in the organic-inorganic composite filler was measured as follows.

<Refractive Index nM of Polymerizable Monomer>

The refractive index nM of the polymerizable monomer (or a mixture of polymerizable monomers) used herein was measured using an Abbe refractive index meter (manufactured by Atago Co., Ltd.) in a thermostatic chamber at 25° C.

<Refractive Index nP of Polymer, Refractive Index nPP of Organic Polymer in Organic-Inorganic Composite Filler>

The refractive index nP of the polymer of the polymerizable monomer (or a mixture of polymerizable monomers) used herein was obtained by measuring the polymer, which had been polymerized under almost the same conditions as the polymerization conditions in a cavity, using an Abbe refractive index meter (manufactured by Atago Co., Ltd.) in a thermostatic chamber at 25° C.

More specifically, the refractive index nPP of the organic polymer in the organic-inorganic composite filler was obtained by measuring the polymer, which had been prepared by polymerizing the polymerizable monomer (or a mixture of polymerizable monomers) used for producing the organic-inorganic composite filler under almost the same conditions as the polymerization conditions in a cavity, using an Abbe refractive index meter (manufactured by Atago Co., Ltd.) in a thermostatic chamber at 25° C.

More specifically, a uniform polymerizable monomer (or a mixture of polymerizable monomers) prepared by mixing 0.2% by mass of CQ, 0.3% by mass of DMBE, and 0.15% by mass of HQME was placed in a mold having a pore of diameter φ7 mm×0.5 mm, and polyester film was pressed against both surfaces. Subsequently, the object was cured by photoirradiation for 30 seconds using a halogen type dental light irradiator (manufacture by Demetron LC, Sybron Dental Specialties Japan, Inc.) with a light quantity of 500 mW/cm$^2$, and then taken out form the die, thus making a cured body of the polymerizable monomer. When the cured body is mounted on an Abbe refractive index meter (manufactured by Atago Co., Ltd.), the sample was not dissolved in order to closely attach the cured body to the surface to be measured, and a solvent having a higher refractive index than the sample (bromonaphthalene) was dropped on the sample, and measurement was carried out.

<Refractive Index nF of Inorganic Filler, Refractive Index nPF of Inorganic Filler in the Organic-Inorganic Composite Filler>

The refractive index nF of the inorganic filler (or a mixture of inorganic fillers) used herein was measured using an Abbe refractive index meter (Atago Co., Ltd.) by an immersion method.

The refractive index nPF of the inorganic filler in the organic-inorganic composite filler was obtained by measuring the inorganic filler (or a mixture of inorganic fillers) used for producing the organic-inorganic composite filler using an Abbe refractive index meter (manufactured by Atago Co., Ltd.) by an immersion method.

More specifically, in a thermostatic chamber at 25° C., in a 100-mL sample bottle, an inorganic filler (or a mixture of inorganic fillers) or 1 g of its surface-treated object were dispersed in 50 mL of anhydrous toluene. 1-bromotoluene was dropped little by little to the dispersion under stirring with a stirrer, and the refractive index of the dispersion at the point when the dispersion became most transparent, and the value thus obtained was recorded as the refractive index of the inorganic filler.

The polymerizable monomer, polymerization initiator, and various additives used in examples and comparative examples of the present invention are de scribed below. For the polymerizable monomer, its refractive index nM and the refractive index nP of the polymer obtained by polymerizing the polymerizable monomer as described above are also given.

[Polymerizable Monomer]
bis-GMA;
2,2-bis[(3-methacryloyloxy-2-hydroxypropyloxy)phenyl]
propane
nM: 1.552
nP: 1.570
3G;
triethylene glycol dimethacrylate
nM: 1.460
nP: 1.510
D-2.6E;
2,2-bis(4-methacryloyloxypolyethoxyphenyl)propane
nM: 1.540
nP: 1.567
U DMA;
1,6-bis(methacrylethyloxycarbonylamino)trimethylhexane
nM: 1.483
nP: 1.509

[Photopolymerization Initiator]
CQ;
camphor quinone
[Heat Polymerization Initiator]
AIBN;
azoisobutyronitrile
[Reducing Compound (Polymerization Promotor)]
DMBE;
N,N-dimethyl-p-ethyl benzoate
[Polymerization Inhibitor]
HQME;
hydroquinone monomethyl ether
[Coloring Agent]
titanium oxide (0.25 μm, white pigment)
Pigment Yellow 95 (yellow pigment)
Pigment Red 166 (red pigment)
Pigment Blue 60 (blue pigment)
[Preparation of Organic Resin Matrix]

The above-described polymerizable monomer was mixed according to the mass ratio given in Table 1, thereby preparing M-1 to M-10 as the polymerizable monomer component (A) used in examples and comparative examples.

Table 1 also shows the refractive index of the polymerizable monomer component (A) at 25° C. measured by the above-described method, and the refractive index nP of the polymer obtained from the monomer component (A) at 25° C.

TABLE 1

|  | Polymerizable monomer (% by mass) | Refractive index nM (25° C.) | Refractive index nP (25° C.) |
|---|---|---|---|
| M-1 | bis-GMA(60)/3G(40) | 1.515 | 1.546 |
| M-2 | UDMA(100) | 1.483 | 1.509 |
| M-3 | bis-GMA(52)/3G(48) | 1.508 | 1.541 |
| M-4 | bis-GMA(30)/D2.6E(40)/3G(30) | 1.520 | 1.551 |
| M-5 | bis-GMA(90)/3G(10) | 1.543 | 1.564 |
| M-6 | bis-GMA(47)/3G(53) | 1.503 | 1.538 |
| M-7 | bis-GMA(70)/D2.6E(20)/3G(10) | 1.540 | 1.563 |
| M-8 | bis-GMA(24)/D2.6E(12)/3G(40)/UDMA(24) | 1.500 | 1.531 |
| M-9 | bis-GMA(40)/3G(40)/UDMA(20) | 1.501 | 1.534 |
| M-10 | bis-GMA(9)/3G(41)/UDMA(50) | 1.480 | 1.515 |

[Inorganic Filler and Inorganic Filler in Organic-Inorganic Composite Filler]

For the inorganic fillers F-1 to F-12 used in examples and comparative examples, their constitution, particle shape, average particle size, and refractive index nF at 25° C. are shown in Table 2.

The inorganic fillers other than ytterbium fluoride of F-4 were surface-treated with γ-methacryloyloxy propylmethoxysilane, and the refraction indices were measured in the surface-treated state.

TABLE 2

|  | Constitution of inorganic filler (% by mass) | Shape | Average primary particle size [μm] | Refractive index nF (25° C.) | Average uniformity |
|---|---|---|---|---|---|
| F-1 | $SiO_2(79.4)/Zr_2O(19.1)/Na_2O(1.5)$ | Spherical | 0.4 | 1.521 | 0.82 |
| F-2 | $SiO_2(79.3)/Zr_2O(18.8)/Na_2O(1.9)$ | Amorphous | 3.2 | 1.521 | 0.43 |
| F-3 | $SiO_2(80.4)/Zr_2O(20.2)/Na_2O(1.4)$ | Spherical | 0.7 | 1.525 | 0.62 |
| F-4 | $YbF_3$ (purity of 99.5% or more) | Approximately spherical | 0.1 | 1.550 | 0.53 |
| F-5 | $SiO_2(72.9)/Zr_2O(25.5)/Na_2O(1.6)$ | Spherical | 0.2 | 1.542 | 0.92 |
| F-6 | $SiO_2(73.0)/Zr_2O(25.6)/Na_2O(1.4)$ | Amorphous | 3.0 | 1.543 | 0.36 |
| F-7 | $SiO_2(90.8)/Ti_2O(7.9)/Na_2O(1.2)$ | Spherical | 0.3 | 1.504 | 0.88 |
| F-8 | F-1(90)/F-4(10) | Spherical/ Approximately spherical | 0.4 | 1.521(90)/ 1.550(10) | 0.79 |
| F-9 | F-1(95)/F-4 (5) | Spherical/ Approximately spherical | 0.4 | 1.521(95)/ 1.550(5) | 0.81 |
| F-10 | $SiO_2(81.4)/Zr_2O(18.4)/Na_2O(1.2)$ | Spherical | 0.5 | 1.515 | 0.79 |
| F-11 | F-1(60)/F-4(10) | Spherical/ Approximately spherical | 0.4 | 1.521(60)/ 1.550(40) | 0.70 |
| F-12 | F-1(40)/F-4(60) | Spherical/ Approximately spherical | 0.4 | 1.521(40)/ 1.550(60) | 0.65 |

[Organic-Inorganic Composite Filler]

For the organic-inorganic composite fillers CF-1 to CF-12 used in examples and comparative examples, their constitution, particle shape, and average particle size are shown in Table 3.

<Preparation Method of CF-1>

100 g of the inorganic filler F-1 were added to 200 g of water, and its aqueous dispersion was obtained using a circulating mill, SC Mill (manufactured by Nippon Coke & Engineering Co., Ltd.).

On the other hand, 4 g (0.016 mol) of γ-methacryloyloxypropyltrimethoxysilane and 0.003 g of acetic acid were added to 80 g of water, stirred for 1 hour and 30 minutes, thereby obtaining a uniform solution with a pH of 4. This solution was added to the inorganic filler dispersion, and mixed until uniform. Thereafter, the dispersion was fed under lightly mixing on a disk rotating at a high speed, and granulated by a spray drying method.

Spray drying was carried out using a spray dryer TSR-2W (manufactured by Sakamoto Giken K.K.) which includes a rotating disk and uses a centrifugal force for spraying. The rotation speed of the disk was 10000 rpm, and the temperature of the dry air atmosphere was 200° C. Thereafter, the powder obtained by granulation through spray drying was vacuum-dried at 60° C. for 18 hours, thereby obtaining 73 g of spherical aggregates.

Subsequently, 10.0 g of the aggregates was immersed in a polymerizable monomer solution (35.6 g parts by mass of a polymerizable monomer is included in 100 parts by mass of an organic solvent) prepared by mixing 1.78 g of M-2 as a polymerizable monomer, 0.005 g of AIBN as a heat polymerization initiator, and 5.0 g of methanol as an organic solvent. The mixture was sufficiently stirred, and allowed to stand for one hour after confirming the mixture was turned to be a slurry.

The above-described mixture was transferred to a rotary evaporator. Under stirring, the mixture was dried for one hour at a degree of pressure reduction of 10 hPa, and under heating conditions of 40° C. (a warm water bath was used), thereby removing the organic solvent. After removing the organic solvent, a powder with high mobility was obtained. The powder exhibited no aggregability.

The powder thus obtained was heated for one hour under stirring with a rotary evaporator at a reduced pressure of 10 hPa and under heating conditions of 100° C. (an oil bath was used), thereby polymerizing and curing the polymerizable monomer in the powder. This operation provided 8.3 g of a spherical organic-inorganic composite filler composed of spherical aggregates whose surface is covered with an organic polymer.

<Preparation Method of CF-2, CF-4 to CF-12>

They were prepared in the same manner as CF-1, except that the organic polymer component (C1) and the inorganic filler component (C2) were changed to those shown in Table 3.

<Preparation Method of CF-3>

100 g of the inorganic particles F-1 was placed in 200 g of water, thereby obtaining a dispersion of inorganic powder using a circulating mill, SC Mill.

On the other hand, 4 g (0.016 mol) of γ-methacryloyloxypropyltrimethoxysilane and 0.003 g of acetic acid were added to 80 g of water, stirred for one hour and 30 minutes, thereby obtaining a uniform solution with a pH of 4. The solution was added to the inorganic filler dispersion, mixed until uniform. Thereafter, while gently mixing the dispersion, the dispersion was fed on the disk rotating at a high speed, and granulated by a spray drying method. The spray drying operation was carried out using a spray dryer TSR-2W (manufactured by Sakamoto Giken K.K.) which includes a rotating disk and uses a centrifugal force for spraying. The rotational speed of the disk was 10000 rpm, and the temperature of the drying atmosphere air was 200° C. Thereafter, the powder obtained by granulation through spray drying was vacuum-dried at 60° C. for 18 hour, thereby obtaining 73 g of spherical aggregates.

Subsequently, 17.0 g of the aggregates, 3.0 g of M-2 as a polymerizable monomer, and 0.017 g of AIBN as a polymerization initiator were placed in a mortar, and mixed while cracking the spherical aggregates, thereby preparing a pasty mixture. The paste mixture was defoamed under reduced pressure, and polymerized and cured at 100° C. for 30 minutes. The cured product was pulverized with a vibrating ball mill (zirconia ball particle size: 05 mm), and the pulverized product was sifted to remove particles having a particle size of 100 μm or more, thus obtaining 16.2 g of an amorphous organic-inorganic composite filler.

TABLE 3

|  | Organic polymer component (C1) | Inorganic filler component (C2) | Weight ratio (organic polymer component (C1):inorganic filler component (C2)) | Shape | Average primary particle size [μm] | Pore volume [cm$^3$/g] | Average uniformity |
|---|---|---|---|---|---|---|---|
| CF-1 | M-2 | F-1 | 85:15 | Spherical | 5.5 | 0.02 | 0.89 |
| CF-2 | M-2 | F-2 | 75:25 | Spherical | 6.1 | 0.03 | 0.77 |
| CF-3 | M-2 | F-1 | 85:15 | Amorphous | 30.3 | 0.00 | 0.45 |
| CF-4 | M-6 | F-4 | 88:12 | Spherical | 12.2 | 0.12 | 0.61 |
| CF-5 | M-8 | F-6 | 77:23 | Spherical | 21.5 | 0.31 | 0.88 |
| CF-6 | M-10 | F-7 | 96:4 | Spherical | 8.8 | 0.09 | 0.95 |
| CF-7 | M-2 | F-8 | 66:34 | Spherical | 5.9 | 0.07 | 0.72 |
| CF-8 | M-2 | F-9 | 85:15 | Spherical | 6.3 | 0.07 | 0.81 |
| CF-9 | M-6 | F-4 | 85:15 | Spherical | 0.7 | 0.01 | 0.62 |
| CF-10 | M-10 | F-10 | 85:15 | Spherical | 7.7 | 0.09 | 0.84 |
| CF-11 | M-2 | F-11 | 85:15 | Spherical | 7.4 | 0.03 | 0.85 |
| CF-12 | M-2 | F-12 | 85:15 | Spherical | 7.6 | 0.08 | 0.88 |

The measurement methods for transparency, light diffusivity, curing depth, color tone compatibility, average primary particle size, and pore volume of the light curable compositions prepared in examples and comparative examples are as described below.

Transparency of Light Curable Composition and its Cured Body (Contrast Ratio);

Each of the pastes of the light curable compositions prepared in examples and comparative examples was placed in a mold having a pore of 7 mmφ×1 mm, and a polyester film was bonded to both sides under pressure.

The paste of the light curable composition was measured using a color-difference meter ("TC-1800MKII", manufactured by Tokyo Denshoku Co, Ltd.) on background colors of black and white, the Y values of tristimulus values (Yb and Yw) were measured on background colors of black and white, the contrast ratio in an uncured state was calculated by the following formula, and used as the index of transparency of the light curable composition.

The cured body of the light curable composition was cured by photoirradiation for 30 seconds on each side using a halogen type dental light irradiator (Demetron LC, manufactured by Sybron Dental Specialties Japan, Inc.) with a light quantity of 500 mW/cm², and then the cured body was taken out from the mold, and measured using a color-difference meter in the same manner as for the paste of the light curable composition. The contrast ratio was calculated based on the following formula, and used as the index of translucency of the cured body of the light curable composition.

The contrast ratio is an index of transparency, and the closer the contrast ratio to 1, the higher the opaqueness.

Contrast ratio=$Yb$ value when the background color is black/$Yw$ value when the background color is white Light Diffusivity;

A mold made by forming a through hole with a diameter of 30 mm at the center of a plate with a thickness of 0.5 mm was filled with the light curable composition. The light curable composition was cured by sufficient photopolymerization, thereby obtaining a cured body. The cured body was taken out from the mold, immersed in water at 37° C. for 24 hours, thereby obtaining a test piece. The sample piece was measured for luminosity distribution of transmitted light using a goniophotometer (GP-2000, manufactured by Murakami Color Research Laboratory). The degree of diffusion D of light was calculated according to the following formula.

$$D=[\{(I(20)/\cos 20°)+(I(70)/\cos 70°)\}/(2\times I(0))]\times 100$$

Wherein I(0), I(20), and I(70) in the formula represent the intensity of light transmitted in directions of 0°, 20°, and 70° to the light incident direction when light is applied perpendicularly to the surface of the plate-shaped test piece having a thickness of 0.5 mm.

Curing Depth;

Each of the pasty light curable compositions prepared in examples and comparative examples was poured into a SUS mold of φ4 mm in diameter×10 mm in thickness, covered with a 50 μm PET film, and the excessive portion of the paste was extruded.

Thereafter, photoirradiation was carried out for 30 seconds using a halogen type dental light irradiator (Demetron LC, manufactured by Sybron Dental Specialties Japan, Inc.) with a light quantity of 500 mW/cm², thereby curing the paste. The cured body was taken out, the unpolymerized portion of the paste was removed with a plastic spatula, and then the thickness of the uncured portion was measured with a micrometer, and recorded as the curing depth.

Clinically, in order to achieve sufficient curability even in a posterior tooth, the curing depth likely must be double the depth of clinical filling. Specifically, in order to fill to a thickness of 3 mm or more, a curing depth of 6 mm or more is necessary. More preferably, in order to fill to a thickness of 4 mm or more, a curing depth of 8 mm or more be achieved.

Evaluation of Color Tone Compatibility;

Each of the pasty light curable compositions prepared in examples and comparative examples was packed into an artificial posterior tooth having a simulated cavity (4 mmφ×4 mm) (A20A-500, manufactured by Nisshin Dental Products Inc.), and subjected to photoirradiation for 30 seconds using a halogen type dental light irradiator (manufactured by Demetron LC, ESPE) with a light quantity of 500 mW/cm², thereby curing the paste.

The sample including the cured body thus obtained was polished with a polishing material (Sof-Lex Superfine, manufactured by 3M), and the color tone compatibility was evaluated by visual observation according to the following criteria.

⊙: The border between the tooth surface and the cured body (light curable composition) is particularly inconspicuous, and color tone compatibility is high.

○: The border between the tooth surface and the cured body (light curable composition) is inconspicuous, and color tone compatibility is high.

×: The border between the tooth surface and the cured body (light curable composition) is conspicuous, and the restored part is recognizable (the restored part is dark or unnaturally white).

Average Primary Particle Size of Inorganic Filler and Organic-Inorganic Composite Filler;

Using a scanning electron microscope (XL-30SFEG, manufactured by Philips N.V.), the photographs of the inorganic filler and the organic-inorganic composite filler were taken at magnifications of 5000 to 100000 times. Using an image analysis software (IP-1000PC, manufactured by Asahi Kasei Engineering Corporation), the images thus taken were processed, the equivalent circle diameter (particle size), the maximum length, the minimum width, and the number of particles in a unit visual field were determined, and the average primary particle size was calculated. The number of particles of the observation object was 100 or more.

Pore Volume of Organic-Inorganic Composite Filler;

A mercury porosimeter (trade name; "PoreMaster", manufactured by Quantachroma) was used. 0.2 g of the organic-inorganic composite filler was placed in a measurement cell, and the pore volume distribution was measured. The volume in the range of the pore volume distribution pore size of 1 to 500 nm was summed, and recorded as the pore volume.

Bending Strength;

Using a filling device, a paste of a dental curable composition was packed into a stainless steel frame (thickness 2 mm, width 2 mm, and length 25 mm). A polypropylene sheet was pressed against the surface of the charged paste, and the paste was subjected to photoirradiation through the polypropylene sheet. Photoirradiation used a visible light irradiator "Power Light" (trade name; manufactured by Tokuyama Dental Corporation). The irradiation window of the visible light irradiator was adhered to the polypropylene sheet, and light was applied to different points on one surface three times each for 30 seconds so as to light was applied to the whole of the cured body. Subsequently, light was applied from the other surface three times each for 30 seconds in the same manner. Through this operation, the paste was polymerized, and a cured body was obtained.

The cured body was shaped into a prism form of 2×2×25 mm using #800 water-resistant abrasive paper. The sample piece was mounted on a testing machine (trade name "Autograph AG5000D", manufactured by Shimadzu Co., Ltd.), and its 3-point bending breaking strength was measured under test conditions including a span of 20 mm and a cross head speed of 1 mm/minute. Five test pieces were evaluated, and the average was recorded as the bending strength.

Shrinkage Stress;

In a jig connected to a testing machine (trade name "Autograph AG5000D", manufactured by Shimadzu Co., Ltd.), ONE-UP BOND F PLUS was applied to the upper surface of a rod having a diameter of 6 mm and subjected to photoirradiation, the object was covered with a ring, thereby making a simulated cavity having a depth of 4 mm. The simulated cavity was filled with a composite resin, and irradiated with visible light for a predetermined time using a visible ray irradiator "Power Light" (trade name; manufactured by Tokuyama Corp.). At this time, the crosshead fixing the load cell moves downwards due to polymerization shrinkage, but the minute movement was detected with a displacement detector, and the cross head was automatically controlled to prevent its movement. At that time, the power detected by a load cell was recorded as the shrinkage stress.

Example 1

To the matrix M-1 as the polymerizable monomer component (A),
CQ (photopolymerization initiator): 0.2% by mass
DMBE (reducing compound): 0.3% by mass
HQME (polymerization inhibitor): 0.15% by mass were added and mixed together, thereby forming a uniform preparation monomer MM-1.

Subsequently, 100 parts by mass of the inorganic filler F-1 as the component (B) and 100 parts by mass of the organic-inorganic composite filler CF-1 as the component (C) were weighed into a mortar, 100.65 parts by mass of the monomer MM-1 prepared above (including 100 parts by mass of the polymerizable monomer component (A)) were gradually added under red color light, the mixture was thoroughly kneaded in a dark place to obtain a uniform paste, and the paste was defoamed under reduced pressure to remove bubbles, thereby obtaining a light curable composition.

The physical properties of the light curable composition thus obtained were evaluated based on the above-described method. The constitution of the light curable composition is given in Table 4, the difference of the refractive indexes between the components is given in Table 5, and the evaluation results are given in Table 6.

Examples 2 to 14

A light curable composition was prepared in the same manner as in Example 1, except that the type and amount of the polymerizable monomer as the polymerizable monomer component (A), the inorganic filler as the inorganic filler component (B), and the organic-inorganic composite filler as the organic-inorganic composite filler component (C) were changed as given in Table 4, and various physical properties were evaluated. The constitution of the light curable composition thus obtained is given in Table 4, the difference of the refractive indexes of the components is given in Table 5, and the evaluation results are given in Table 6.

TABLE 4

| | Polymerizable monomer component (A) | | | Inorganic filler component (B) | | Organic-inorganic composite filler (C) | | |
|---|---|---|---|---|---|---|---|---|
| | Loading [part by mass] | Refractive index (nM) | Refractive index (nP) | Loading [part by mass] | Refractive index (nF) | Loading [part by mass] | Refractive index (nPF) | Refractive index (nPP) |
| Example 1 | M-1 (100) | 1.515 | 1.546 | F-1 (100) | 1.521 | CF-1 (100) | 1.521 | 1.509 |
| Example 2 | M-1 (100) | 1.515 | 1.546 | F-2 (100) | 1.523 | CF-2 (100) | 1.523 | 1.509 |
| Example 3 | M-1 (100) | 1.515 | 1.546 | F-1 (100) | 1.521 | CF-3 (100) | 1.521 | 1.509 |
| Example 4 | M-3 (100) | 1.508 | 1.541 | F-1 (100) | 1.521 | CF-1 (100) | 1.521 | 1.509 |
| Example 5 | M-4 (100) | 1.520 | 1.541 | F-1 (100) | 1.521 | CF-1 (100) | 1.521 | 1.509 |
| Example 6 | M-1 (100) | 1.515 | 1.546 | F-3 (100) | 1.525 | CF-1 (100) | 1.521 | 1.509 |
| Example 7 | M-5 (100) | 1.543 | 1.564 | F-4 (100) | 1.550 | CF-4 (100) | 1.550 | 1.538 |
| Example 8 | M-7 (100) | 1.540 | 1.563 | F-5 (100) | 1.542 | CF-5 (100) | 1.543 | 1.531 |
| Example 9 | M-9 (100) | 1.501 | 1.534 | F-7 (100) | 1.504 | CF-6 (100) | 1.504 | 1.515 |
| Example 10 | M-1 (100) | 1.515 | 1.546 | F-8 (100) | 1.521 (90)/ 1.550 (10) | CF-7 (100) | 1.521 (90)/ 1.550 (10) | 1.509 |
| Example 11 | M-1 (100) | 1.515 | 1.546 | F-9 (100) | 1.521 (95)/ 1.550 (5) | CF-8 (100) | 1.521 (95)/ 1.550 (5) | 1.509 |
| Example 12 | M-7 (100) | 1.540 | 1.563 | F-5 (150) | 1.542 | CF-5 (150) | 1.543 | 1.531 |
| Example 13 | M-7 (100) | 1.540 | 1.563 | F-5 (150) | 1.542 | CF-5 (200) | 1.543 | 1.531 |
| Example 14 | M-5 (100) | 1.543 | 1.564 | F-4 (100) | 1.550 | CF-9 (100) | 1.550 | 1.538 |

TABLE 5

|  | nM-nF | nM-nPF | nM-nPP | nP-nF | nP-nPF | nP-nPP | nPP-nPF | nF-nPF | nF-nPP |
|---|---|---|---|---|---|---|---|---|---|
| Example 1 | −0.006 | −0.006 | 0.006 | 0.025 | 0.025 | 0.037 | −0.012 | 0.000 | 0.012 |
| Example 2 | −0.008 | −0.008 | 0.006 | 0.023 | 0.023 | 0.037 | −0.014 | 0.000 | 0.014 |
| Example 3 | −0.006 | −0.006 | 0.006 | 0.025 | 0.025 | 0.037 | −0.012 | 0.000 | 0.012 |
| Example 4 | −0.013 | −0.013 | −0.001 | 0.020 | 0.020 | 0.032 | −0.012 | 0.000 | 0.012 |
| Example 5 | −0.001 | −0.001 | 0.011 | 0.030 | 0.030 | 0.042 | −0.012 | 0.000 | 0.012 |
| Example 6 | −0.010 | −0.006 | 0.006 | 0.021 | 0.025 | 0.037 | −0.012 | 0.004 | 0.016 |
| Example 7 | −0.007 | −0.007 | 0.005 | 0.014 | 0.014 | 0.026 | −0.012 | 0.000 | 0.012 |
| Example 8 | −0.002 | −0.003 | 0.009 | 0.021 | 0.020 | 0.032 | −0.012 | −0.001 | 0.011 |
| Example 9 | −0.003 | −0.003 | −0.014 | 0.030 | 0.030 | 0.019 | 0.011 | 0.000 | −0.011 |
| Example 10 | −0.006/ −0.035 | −0.006/ −0.035 | 0.006 | 0.025/ −0.004 | 0.025/ −0.004 | 0.037 | −0.012/ −0.041 | 0.000 | 0.012/ 0.041 |
| Example 11 | −0.006/ −0.035 | −0.006/ −0.035 | 0.006 | 0.025/ −0.004 | 0.025/ −0.004 | 0.037 | −0.012/ −0.041 | 0.000 | 0.012/ 0.041 |
| Example 12 | −0.002 | −0.003 | 0.009 | 0.021 | 0.020 | 0.032 | −0.012 | −0.001 | 0.011 |
| Example 13 | −0.002 | −0.003 | 0.009 | 0.021 | 0.020 | 0.032 | −0.012 | −0.001 | 0.011 |
| Example 14 | −0.007 | −0.007 | 0.005 | 0.014 | 0.014 | 0.026 | −0.012 | 0.000 | 0.012 |

TABLE 6

|  | Contrast ratio of composition | Contrast ratio of cured body | Degree of light diffusion | Curing depth [mm] | Color tone compatibility | Bending strength [Mpa] | Shrinkage stress [Mpa] |
|---|---|---|---|---|---|---|---|
| Example 1 | 0.23 | 0.38 | 41 | 9.1 | ⊚ | 155 | 0.62 |
| Example 2 | 0.26 | 0.38 | 41 | 8.5 | ⊚ | 148 | 0.81 |
| Example 3 | 0.22 | 0.39 | 41 | 9.3 | ⊚ | 108 | 1.22 |
| Example 4 | 0.30 | 0.34 | 35 | 6.8 | ○ | 153 | 0.65 |
| Example 5 | 0.21 | 0.41 | 44 | 10< | ⊚ | 154 | 0.66 |
| Example 6 | 0.27 | 0.36 | 38 | 8.3 | ⊚ | 153 | 0.64 |
| Example 7 | 0.25 | 0.33 | 24 | 8.9 | ○ | 137 | 0.68 |
| Example 8 | 0.20 | 0.35 | 34 | 10< | ⊚ | 133 | 0.63 |
| Example 9 | 0.24 | 0.35 | 20 | 8.8 | ○ | 141 | 0.63 |
| Example 10 | 0.25 | 0.38 | 41 | 8.8 | ⊚ | 143 | 0.66 |
| Example 11 | 0.23 | 0.37 | 41 | 9.0 | ⊚ | 144 | 0.65 |
| Example 12 | 0.21 | 0.34 | 33 | 10< | ○ | 135 | 0.63 |
| Example 13 | 0.21 | 0.34 | 32 | 10< | ○ | 134 | 0.64 |
| Example 14 | 0.24 | 0.34 | 26 | 8.7 | ○ | 141 | 0.71 |

As understood from the results of Examples 1 to 14, when the relationship between the refractive index nM, nP, and nF satisfies the conditions (X1) defined in the present invention, the light curable composition has high transparency, achieves a high curing depth, the cured body to be obtained has appropriate translucency, and the color tone compatibility with teeth is good. Particularly, Examples 1 to 3 and 5 to 14 having a contrast ratio of 0.27 or less before polymerization achieved a particularly deep curing depth of 8 mm or more, and exhibited good color tone compatibility.

Comparative Examples 1 to 5

A light curable composition was prepared in the same manner as in Example 1, except that the type of the polymerizable monomer as the polymerizable monomer component (A), the inorganic filler as the inorganic filler component (B), and the organic-inorganic composite filler as the organic-inorganic composite filler component (C) were changed as given in Table 7, and various physical properties were evaluated. The constitution of the light curable composition thus obtained is given in Table 7, the difference of the refractive indexes of the components is given in Table 8, and the evaluation results are given in Table 9.

TABLE 7

|  | Polymerizable monomer component (A) | | | Inorganic filler component (B) | | Organic-inorganic composite filler (C) | | |
|---|---|---|---|---|---|---|---|---|
|  | Loading [part by mass] | Refractive index (nM) | Refractive index (nP) | Loading [part by mass] | Refractive index (nF) | Loading [part by mass] | Refractive index (nPF) | Refractive index (nPP) |
| Comparative Example 1 | M-9 (100) | 1.501 | 1.534 | F-1 (100) | 1.521 | CF-1 (100) | 1.521 | 1.509 |
| Comparative Example 2 | M-2 (100) | 1.483 | 1.509 | F-5 (100) | 1.542 | CF-10 (100) | 1.515 | 1.509 |

TABLE 7-continued

| | Polymerizable monomer component (A) | | | Inorganic filler component (B) | | Organic-inorganic composite filler (C) | | |
|---|---|---|---|---|---|---|---|---|
| | Loading [part by mass] | Refractive index (nM) | Refractive index (nP) | Loading [part by mass] | Refractive index (nF) | Loading [part by mass] | Refractive index (nPF) | Refractive index (nPP) |
| Comparative Example 3 | M-4 (100) | 1.520 | 1.551 | F-5 (100) | 1.542 | CF-1 (100) | 1.521 | 1.509 |
| Comparative Example 4 | M-1 (100) | 1.515 | 1.546 | F-11 (100) | 1.521 (60)/ 1.550 (40) | CF-11 (100) | 1.521 (60)/ 1.550 (40) | 1.509 |
| Comparative Example 5 | M-1 (100) | 1.515 | 1.546 | F-12 (100) | 1.521 (40)/ 1.550 (60) | CF-12 (100) | 1.521 (40)/ 1.550 (60) | 1.509 |

TABLE 8

| | nM-nF | nM-nPF | nM-nPP | nP-nF | nP-nPF | nP-nPP | nPP-nPF | nF-nPF | nF-nPP |
|---|---|---|---|---|---|---|---|---|---|
| Comparative Example 1 | −0.020 | −0.020 | −0.008 | 0.013 | 0.013 | 0.025 | −0.012 | 0.000 | 0.012 |
| Comparative Example 2 | −0.059 | −0.032 | −0.026 | −0.033 | −0.006 | 0.000 | −0.006 | 0.027 | 0.033 |
| Comparative Example 3 | −0.022 | −0.001 | 0.011 | 0.009 | 0.030 | 0.042 | −0.012 | 0.021 | 0.033 |
| Comparative Example 4 | −0.006/ −0.035 | −0.006/ −0.035 | 0.006 | 0.0025/ −0.004 | 0.025/ −0.004 | 0.037 | −0.012/ −0.041 | 0 | 0.012/ 0.041 |
| Comparative Example 5 | −0.006/ −0.035 | −0.006/ −0.035 | 0.006 | 0.0025/ −0.004 | 0.025/ −0.004 | 0.037 | −0.012/ −0.041 | 0 | 0.012/ 0.041 |

TABLE 9

| | Contrast ratio of composition | Contrast ratio of cured body | Degree of light diffusion | Curing depth [mm] | Color tone compatibility | Bending strength [Mpa] | Shrinkage stress [Mpa] |
|---|---|---|---|---|---|---|---|
| Comparative Example 1 | 0.34 | 0.34 | 23 | 5.7 | X | 158 | 0.63 |
| Comparative Example 2 | 0.20 | 0.38 | 8 | 10.0 | Δ | 142 | 0.64 |
| Comparative Example 3 | 0.32 | 0.39 | 44 | 5.9 | ◉ | 154 | 0.63 |
| Comparative Example 4 | 0.37 | 0.42 | 43 | 5.8 | ◉ | 149 | 0.66 |
| Comparative Example 5 | 0.42 | 0.44 | 43 | 5.2 | ◉ | 143 | 0.67 |

As understood from Comparative Examples 1 to 5, when the relationship between the refractive indexes nM, nP, and nF did not satisfy the conditions (X1) defined in the present invention, the contrast ratio before polymerization was 0.35 or more, transparency was poor, the curing depth was small or light diffusivity was small, and the color tone compatibility was low.

Examples 15 to 18, Reference Examples 1, 2

The coloring agent given in Table 10 was added to the pastes of the light curable compositions obtained in Example 5 and Example 8, and thoroughly kneaded in a dark place. The colored pastes were defoamed under reduced pressure to remove bubbles, thereby obtaining light curable compositions including a coloring agent. Among the coloring agents added, titanium dioxide as a white pigment is regarded as an inorganic filler, but its amount is up to 200.0 ppm (0.02%) in Examples 15 to 18 and Reference Examples 1 and 2. In Example 5 and Example 8, 100% of the inorganic filler satisfies the conditions (X1), so that 90% or more of the inorganic fillers of Examples 15 to 18 and Reference Examples 1 and 2 satisfies the conditions (X1) even in consideration of the coloring agent added.

Physical properties of the light curable compositions thus obtained were evaluated based on the above-described method, and the results are given in Table 11.

TABLE 10

| | Paste | (E) Coloring agent [ppm] | | | | |
| --- | --- | --- | --- | --- | --- | --- |
| | | White pigment | Yellow pigment | Red pigment | Blue pigment | Total |
| Example 15 | Example 5 | 0.0 | 10.5 | 3.1 | 1.4 | 15.0 |
| Example 16 | Example 8 | 0.0 | 10.1 | 3.1 | 1.5 | 14.7 |
| Example 17 | Example 5 | 55.0 | 10.2 | 3.2 | 1.3 | 69.7 |
| Example 18 | Example 8 | 65.0 | 10.2 | 3.0 | 1.4 | 79.6 |
| Reference Example 1 | Example 5 | 140.0 | 0.0 | 0.0 | 0.0 | 140.0 |
| Reference Example 2 | Example 8 | 200.0 | 0.0 | 0.0 | 0.0 | 200.0 |

TABLE 11

| | Contrast ratio of composition | Contrast ratio of cured body | Degree of light diffusion | Curing depth [mm] | Color tone compatibility | Bending strength [Mpa] | Shrinkage stress [Mpa] |
| --- | --- | --- | --- | --- | --- | --- | --- |
| Example 15 | 0.23 | 0.45 | 44 | 10< | ⊚ | 155 | 0.65 |
| Example 16 | 0.21 | 0.41 | 34 | 10< | ⊚ | 135 | 0.63 |
| Example 17 | 0.29 | 0.53 | 43 | 6.6 | ⊚ | 157 | 0.66 |
| Example 18 | 0.30 | 0.52 | 33 | 6.4 | ⊚ | 136 | 0.63 |
| Reference Example 1 | 0.47 | 0.63 | 40 | 2.8 | Δ | 161 | 0.65 |
| Reference Example 2 | 0.47 | 0.59 | 30 | 3.1 | Δ | 139 | 0.63 |

As understood from the results of Examples 15 to 18, a sufficient curing depth was achieved when the contrast ratio before polymerization was 0.30 or less, even if the light curable composition included a coloring agent. Additionally, the color tone compatibility was good.

On the other hand, as understood from the results of Reference Examples 1 and 2, the curing depth was small when the content of the white pigment was high and the contrast ratio before polymerization was more than 0.30. Additionally, the contrast ratio of the cured body was high, and the color tone compatibility was low.

The invention claimed is:

1. A light curable composition comprising:
a polymerizable monomer component (A);
an inorganic filler component (B) having an average particle size of 0.07 μm or more;
an organic-inorganic composite filler component (C) including an inorganic filler component (C1) and an organic polymer component (C2) and having an average particle size of 0.5 μm or more;
a photopolymerization initiator (D); and
0.001 to 80 ppm of a coloring agent (E) per the light curable composition,
wherein the light curable composition includes the inorganic filler component (B) and the organic-inorganic composite filler component (C) in a total amount of 100 to 1500 parts by mass with reference to 100 parts by mass of the polymerizable monomer component (A),
the polymerizable monomer component (A), 90% by mass or more of the inorganic filler component (B), and 90% by mass or more of the organic-inorganic composite filler component (C) are selected so as to satisfy conditions (X2) represented by the following formula (2a-a' to 2c-b')

$$-0.010 < nM-nF < 0.010 \quad (2a\text{-}a')$$

$$-0.010 < nM-nPF < 0.010 \quad (2a\text{-}b')$$

$$-0.010 < nM-nPP < 0.010 \quad (2a\text{-}c')$$

$$0.010 < |nP-nF| < 0.040 \quad (2b\text{-}a')$$

$$0.010 < |nP-nPF| < 0.040 \quad (2b\text{-}b')$$

$$0.010 < |nP-nPP| < 0.040 \quad (2b\text{-}c')$$

$$0.010 < |nPP-nPF| < 0.020 \quad (2b\text{-}d')$$

$$-0.015 < nF-nPF < 0.015 \quad (2c\text{-}a')$$

$$-0.015 < nF-nPP < 0.015 \quad (2c\text{-}b')$$

(wherein
nM represents a refractive index of the polymerizable monomer component (A) at 25° C.
nP represents a refractive index of a polymer obtained by polymerizing the polymerizable monomer component (A) at 25° C.,
nF represents a refractive index of the inorganic filler component (B) at 25° C.,
nPF represents a refractive index of the inorganic filler component (C1) in the organic-inorganic composite filler component (C) at 25° C., and
nPP represents a refractive index of the organic polymer component (C2) in the organic-inorganic composite filler component (C) at 25° C.),
a contrast ratio measured in an uncured state having a thickness of 1 mm is 0.30 or less, and a contrast ratio measured in a cured body state having a thickness of 1 mm is 0.33 or more, and
a degree of diffusion D of a cured body having a thickness of 0.5 mm defined by the following formula is 15 or more, $$D = (((I(20)/\cos 20°) + (I(70)/\cos 70°)/(2 \times I(0))) \times 100$$

(wherein I(W/sr) represents intensity of light passing through a sample, I(0), I(20), and I(70) represent intensity of light at angles of 0, 20, and 70, respectively, with respect to an incident direction of light).

2. The light curable composition of claim 1, wherein a total amounts of the polymerizable monomer component (A), the inorganic filler component (B), and the organic-inorganic composite filler component (C) satisfy the conditions (X2).

3. The light curable composition of claim 1, comprising a plurality of kinds of polyfunctional (meth)acryl compounds as the polymerizable monomer component (A), and has a refractive index (25° C.) of 1.48 to 1.55.

4. The light curable composition of claim 3, wherein the plurality of kinds of polyfunctional (meth)acryl compounds includes a combination of a polyfunctional aromatic (meth)acrylate and a polyfunctional aliphatic (meth)acrylate.

5. The light curable composition of claim 4, wherein the polyfunctional aromatic (meth)acrylate is 2,2-bis[(3-methacryloyloxy-2-hydroxypropyloxy)phenyl]propane and/or 2,2-bis[(4-methacryloyloxypolyethoxyphenyl)propane, and the polyfunctional aliphatic (meth)acrylate is triethylene glycol dimethacrylate and/or triethylene 1,6-bis(methacrylethyloxycarbonylamino)trimethylhexane.

6. The light curable composition of claim 1, wherein the organic-inorganic composite filler component (C) is an organic-inorganic composite filler including aggregates prepared by agglomerating inorganic primary particles having an average particle size of 10 to 1000 nm, organic resin phases including a polymerized cured body of a polymerizable monomer which covers a surface of each inorganic primary particle and mutually binding inorganic primary particles, and aggregation gaps with a micropore volume of 0.01 to 0.30 $cm^3/g$ formed between the organic resin phases, the volume being measured by measurement of pores with a pore diameter of 1 to 500 nm as measured by mercury porosimetry.

7. The light curable composition of claim 1, wherein a contrast ratio of 0.30 or less as measured in an uncured state having a thickness of 1 mm, and a contrast ratio of 0.55 or less as measured in a cured body state having a thickness of 1 mm.

8. A dental restoring filler comprising the light curable composition of claim 1.

* * * * *